(12) United States Patent
Salciccioli et al.

(10) Patent No.: US 10,059,641 B2
(45) Date of Patent: Aug. 28, 2018

(54) CONVERSION OF NON-AROMATIC HYDROCARBON

(71) Applicant: ExxonMobil Chemical Patents Inc., Baytown, TX (US)

(72) Inventors: Michael Salciccioli, Houston, TX (US); Glenn C. Wood, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/240,793

(22) Filed: Aug. 18, 2016

(65) Prior Publication Data

US 2017/0088489 A1 Mar. 30, 2017

Related U.S. Application Data

(60) Provisional application No. 62/247,795, filed on Oct. 29, 2015, provisional application No. 62/232,609, filed on Sep. 25, 2015.

(30) Foreign Application Priority Data

Nov. 19, 2015 (EP) .................................... 15195311
Dec. 3, 2015 (EP) .................................... 15197700

(51) Int. Cl.
C07C 2/76 (2006.01)
C07C 2/86 (2006.01)
C07C 5/27 (2006.01)
C07C 7/04 (2006.01)
C07C 7/12 (2006.01)
(Continued)

(52) U.S. Cl.
CPC ................ *C07C 2/864* (2013.01); *C07C 2/76* (2013.01); *C07C 5/2732* (2013.01); *C07C 6/123* (2013.01); *C07C 7/04* (2013.01); *C07C 7/12* (2013.01); *C07C 7/13* (2013.01); *C07C 7/14* (2013.01)

(58) Field of Classification Search
None
See application file for complete search history.

(56) References Cited

U.S. PATENT DOCUMENTS 3,894,102 A 7/1975 Chang et al.
3,894,103 A 7/1975 Chang et al.
(Continued)

FOREIGN PATENT DOCUMENTS

EP 0293032 6/1987
WO 97/17290 5/1997
(Continued)

OTHER PUBLICATIONS

Choudhary et al., "Influence of space velocity on product selectivity and distribution of aromatics in propane aromatization over H-GaAlMFI zeolite", Journal of Molecular Catalysis A: Chemical, vol. 246, pp. 79-84 (2006).
(Continued)

*Primary Examiner* — Tam M Nguyen

(57) ABSTRACT

Systems and methods are provided for converting alkane while generating improved yields of desirable aromatics and/or improved selectivity for forming desired aromatics, such as para-xylene (p-xylene). Aromatics generated during the aromatic formation process can be alkylated to form xylenes with improved yield and/or improved selectivity.

19 Claims, 3 Drawing Sheets

(51) Int. Cl.
*C07C 7/13* (2006.01)
*C07C 7/14* (2006.01)
*C07C 6/12* (2006.01)

(56) References Cited

U.S. PATENT DOCUMENTS

| | | |
|---|---|---|
| 3,894,104 A | 7/1975 | Chang et al. |
| 3,894,107 A | 7/1975 | Butter et al. |
| 3,960,978 A | 6/1976 | Givens et al. |
| 4,016,218 A | 4/1977 | Haag et al. |
| 4,021,502 A | 5/1977 | Plank et al. |
| 4,035,430 A | 7/1977 | Dwyer et al. |
| 4,058,576 A | 11/1977 | Chang et al. |
| 4,150,062 A | 4/1979 | Garwood et al. |
| 4,227,992 A | 10/1980 | Garwood et al. |
| 4,439,409 A | 3/1984 | Puppe et al. |
| 4,456,781 A | 6/1984 | Marsh et al. |
| 4,528,412 A | 7/1985 | Steacy |
| 4,788,364 A | 11/1988 | Harandi |
| 4,826,667 A | 5/1989 | Zones et al. |
| 4,855,522 A | 8/1989 | Diaz |
| 4,954,325 A | 9/1990 | Rubin et al. |
| 5,043,502 A | 8/1991 | Martindale et al. |
| 5,227,557 A | 7/1993 | Bournonville et al. |
| 5,236,575 A | 8/1993 | Bennett et al. |
| 5,250,277 A | 10/1993 | Kresge et al. |
| 5,362,697 A | 11/1994 | Fung et al. |
| 5,633,417 A | 5/1997 | Beck et al. |
| 5,675,047 A | 10/1997 | Beck et al. |
| 5,750,820 A | 5/1998 | Wei |
| 5,936,135 A | 8/1999 | Choudhary et al. |
| 6,077,498 A | 6/2000 | Diaz Cabanas et al. |
| 6,617,275 B1 | 9/2003 | Sharma et al. |
| 6,670,517 B1 | 12/2003 | Abichandani et al. |
| 7,022,888 B2 | 4/2006 | Choudhary et al. |
| 8,344,197 B2 | 1/2013 | Lattner et al. |
| 8,378,162 B2 | 2/2013 | Iaccino et al. |
| 8,529,757 B2 | 9/2013 | Go et al. |
| 8,697,929 B2 | 4/2014 | Ou et al. |
| 8,835,706 B2 | 9/2014 | Iyer et al. |
| 2007/0259972 A1 | 11/2007 | Lattner et al. |
| 2008/0033218 A1 | 2/2008 | Lattner et al. |
| 2009/0209794 A1 | 8/2009 | Lauritzen et al. |
| 2011/0132803 A1 | 6/2011 | Umansky et al. |
| 2014/0100398 A1* | 4/2014 | Jin .................. C07C 2/76 585/254 |
| 2015/0175499 A1 | 6/2015 | Ou et al. |

FOREIGN PATENT DOCUMENTS

| | | |
|---|---|---|
| WO | 2010/140005 | 12/2010 |
| WO | 2013/169465 | 11/2013 |

OTHER PUBLICATIONS

Choudhary et al., "Effect of temperature on the product selectivity and aromatics distribution in aromatization of propane over H-GaAlMFI zeolite", Microporous and Mesoporous Materials, vol. 70, pp. 37-42, (2004).

Giannetto et al., "Transformation of LPG into Aromatic Hydrocarbons and Hydrogen over Zeolite Catalysts", Catalysis Reviews-Science and Engineering, vol. 36, issue 2, pp. 271-304, (1994).

* cited by examiner

CONVERSION OF NON-AROMATIC HYDROCARBON

CROSS-REFERENCE TO RELATED APPLICATIONS

This invention claims priority to and the benefit of U.S. Patent Application Ser. No. 62/232,609 filed Sep. 25, 2015; U.S. Patent Application Ser. No. 62/247,795, filed Oct. 29, 2015; European Patent Application No. 15195311.4 filed Nov. 19, 2015; and European Patent Application No. 15197700.6 filed Dec. 3, 2015, all of which are incorporated by reference in their entireties. The following related cases are also incorporated by reference in their entireties: U.S. Patent Application Ser. No. 62/234,262; European Patent Application No. 15195314.8; U.S. Patent Application Ser. No. 62/234,240; European Patent Application No. 15197698.2; U.S. Patent Application Ser. No. 62/248,374; European Patent Application No. 15197702.2; U.S. Patent Application Ser. No. 62/253,268; U.S. Patent Application Ser. No. 62/298,655; European Patent Application No. 16167672.1; U.S. Patent Application Ser. No. 62/326,918; European Patent Application No. 16175163.1 U.S. Patent Application Ser. No. 62/299,730; European Patent Application No. 16167395.9; U.S. Patent Application Ser. No. 62/313,288; European Patent Application No. 16173587.3; U.S. Patent Application Ser. No. 62/313,306 and European Patent Application No. 16173980.0.

FIELD OF THE INVENTION

Systems and methods are provided for converting non-aromatic hydrocarbon to aromatics.

BACKGROUND OF THE INVENTION

Conversion of aliphatic compounds to aromatics is an ongoing area of study for chemical manufacture. Certain aromatic compounds, such as para-xylene, have a relatively high commercial value. Processes that can allow formation of aromatics from feed streams that primarily have fuel value, such as natural gas or fuel gas, can be beneficial if the conversion to aromatics can be performed at a reasonable cost. Due to the relatively low activity of alkane compounds in processes for direct conversion to aromatics, additional improvements in processes for conversion of alkane to aromatics are desirable.

U.S. Pat. No. 5,043,502 describes a method for dehydroaromatization of $C_2$-$C_5$ aliphatic hydrocarbons to form aromatics. Para-xylene is produced both from the dehydroaromatization reaction and from subsequent methylation of toluene generated by the dehydroaromatization reaction. Benzene is also produced from dehydroaromatization and is described as being methylated to toluene during the subsequent methylation.

Other conventional processes can utilize feeds containing methane. Although methane is abundant, its relative inertness has limited its utility in these conversion processes. For example, oxidative coupling methods generally involve highly exothermic methane combustion reactions, frequently require expensive oxygen generation facilities, and produce large quantities of low value carbon oxides. Non-oxidative methane aromatization is equilibrium-limited, and temperatures ≥about 800° C. are needed for methane conversions greater than a few percent.

To obviate these problems, catalytic processes have been proposed for co-converting methane and one or more co-reactants to higher hydrocarbon, such as aromatics. For example, U.S. Pat. No. 5,936,135 discloses reacting methane at a temperature in the range of 300° C. to 600° C. with (i) a $C_{2-10}$ olefin and/or (ii) a $C_{2-10}$ paraffin in the presence of a bifunctional pentasil zeolite catalyst, having strong dehydrogenation and acid sites, to produce aromatics. The preferred mole ratio of olefin and/or higher paraffin to methane and/or ethane in the feed ranges from about 0.2 to about 2.0.

Other processes utilize organic oxygenate as a co-reactant for the non-oxidative methane conversion to produce higher hydrocarbon, including aromatics. For example, U.S. Pat. No. 7,022,888 discloses a process for the non-oxidative conversion of methane simultaneously with the conversion of an organic oxygenate, represented by a general formula: $C_nH_{2n+1}OC_mH_{2m+1}$, wherein C, H and O are carbon, hydrogen and oxygen, respectively; n is an integer having a value between 1 and 4; and m is an integer having a value between zero and 4. However, since these co-reactants are themselves valuable commodities, there is interest in developing alternative routes for the conversion of methane and/or other low molecular weight hydrocarbons into aromatics, particularly via routes that allow incorporation of more feed hydrocarbon into the aromatic product. It is desirable for such conversion reactions to operate over a broad molar ratio range of methane to other hydrocarbons in the feed.

SUMMARY OF THE INVENTION

The invention concerns processes which include (a) converting non-aromatic hydrocarbon to an aromatic product and (ii) methylating the aromatic product to produce para-xylene. The invention relates to the discovery that producing fewer $C_8$ aromatics during the non-aromatics conversion results in a desirable increase in para-xylene produced by the combined conversion-methylation process. While not wishing to be bound by any theory or model, it is believed that increasing the selectivity for $C_8$ aromatic hydrocarbon during aromatic formation process also leads to increased formation of ethylbenzene, which decreases the amount of para-xylene produced during methylation. It has also been discovered that a reduced size can be achieved for separators used in recovery of a desired xylene fraction by forming separate $C_8$ intermediate streams from the aromatic effluent of the non-aromatic hydrocarbon conversion and the para-xylene-containing effluent of the methylation. Forming separate $C_8$ intermediate streams and avoiding dilution of a stream with a higher concentration of $C_8$ aromatic hydrocarbon with a lower concentration stream allows for introduction of $C_8$ aromatic streams having different $C_8$ aromatic hydrocarbon concentrations at different locations in a xylene separation process vessel, which increases separation efficiency and can further allow for a decrease in the hydraulic capacity of separation equipment. More particularly with respect to the aromatization, it has surprisingly been found that producing >20 wt. % of ethylbenzene based on the total weight of aromatic hydrocarbon in the aromatic formation effluent ethylbenzene during the aromatics formation process lessens the recovery of xylenes, particularly paraxylene from the method. More particularly with respect to the methylation, it has surprisingly been found that producing a first lower boiling intermediate stream containing at least about 50 wt. % of benzene has been found to increase $C_{7+}$ aromatic hydrocarbon production, particularly para-xylene production, during the methylation. It has also been found that producing an aromatics formation effluent having a toluene to benzene molar ratio of at least 1.4 reduces or even minimizes ethylbenzene formation during xylene methylation.

Systems and apparatus for carrying out any of these methods are within the scope of the invention. References to a "$C_x$ aromatics stream" or a "$C_x$ intermediate stream" correspond to a stream containing at least 50 wt. % of the named type of aromatic, such as a $C_8$ aromatic for a $C_8$ intermediate stream.

DETAILED DESCRIPTION OF THE EMBODIMENTS

Figure 1:
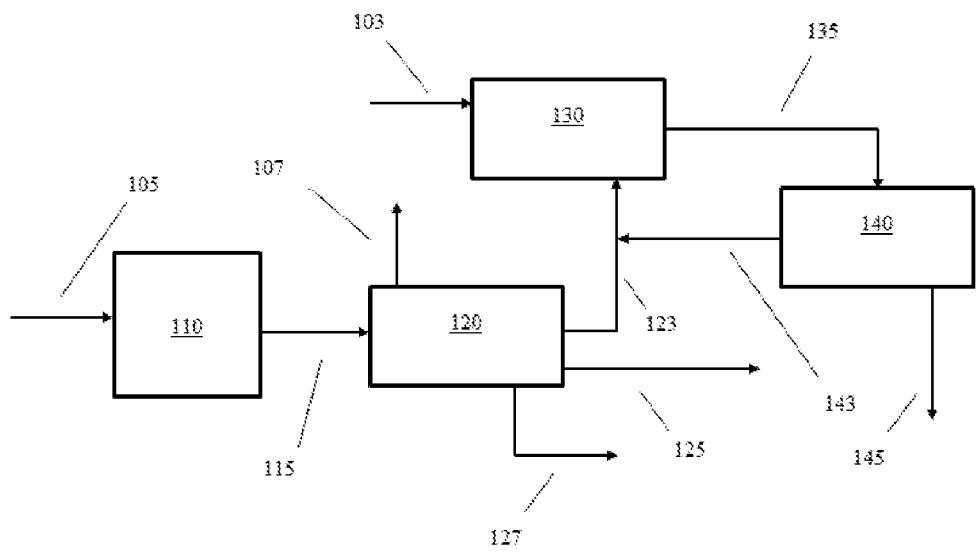
FIG. 1 schematically shows an example of a reaction system for converting a feed to form aromatic hydrocarbon.

In various aspects, systems and methods are provided for converting non-aromatic hydrocarbon with improved yields of desirable aromatic hydrocarbon and/or improved selectivity for forming desired aromatic hydrocarbon, e.g., xylenes such as para-xylene (p-xylene). Certain aspects of the invention are based on the discovery that a decrease in $C_8$ hydrocarbon yield during aromatic formation lead to an increase in the yield of xylenes. Surprisingly, increasing the yield of benzene and $C_7$ aromatic hydrocarbon generated during aromatic formation and/or decreasing the yield of $C_8$ aromatic hydrocarbon and/or the amount of ethylbenzene in the aromatic product has been found to increase the amount of para-xylene produced by the overall process. The benzene and/or $C_7$ aromatic hydrocarbon in the aromatic formation product can be alkylated to form xylenes with improved yield and/or improved selectivity to produce a methylated aromatic product having an increased xylene concentration and a decreased ethylbenzene concentration compared to conventional aromatic formation processes. It has been found that as a result of the relatively low aromatic hydrocarbon yield of the aromatic formation process, preferentially producing additional benzene and then methylating the benzene to form xylene can provide a method having a higher net yield of carbons included in a product aromatics fraction relative to the amount of carbons included in the feed's non-aromatic hydrocarbon as compared with conventional processes. It has also been discovered that lessening or even minimizing the amount of $C_8$ aromatic hydrocarbon in the aromatic formation product allows greater use of a liquid-phase isomerization system for xylene isomerization instead of less desired vapor-phase isomerization. Additionally or alternately, improved yields of para-xylene and/or selectivity for para-xylene can be achieved by generating xylenes using a multi-stage process while maintaining the separate identity of the $C_8$ streams generated from the multiple process stages. Instead of mixing the $C_8$ products from each stage together, the different stage products can be passed into a xylene separation stage at different locations to take advantage of the different product compositions. This can reduce the needed size and/or capacity of xylene separation equipment, while allowing for an improved overall yield and/or selectivity for para-xylene formation.

In some aspects, one or more of the above benefits can be achieved based on forming aromatic hydrocarbon from at least a portion of the feed's non-aromatic hydrocarbon. Although conventional catalytic reforming of non-aromatic hydrocarbon in a naphtha feed is within the scope of the invention, the invention is more generally applicable, and is compatible with a wide variety of aromatic formation processes including those based on dehydrocyclization of paraffinic hydrocarbon, normal olefin, and iso-olefin. Relative to conventional naphtha reforming, such dehydrocyclization exhibits greater selectivity for forming xylene in preference to ethylbenzene as part of the $C_8$ products, and are therefore particularly suitable for producing the aromatics formation effluent.

In certain aspects, the invention relates to a method for converting the feed's non-aromatic hydrocarbon to a desired aromatic stream. The method includes a series of processes, typically at least one aromatic formation process and at least one methylation process. Each process can include one or more stages, such as reaction stages or separation stages. For example, an initial process can correspond to an aromatic formation process, where compounds containing aromatic rings are formed from non-aromatic hydrocarbon. A first separation process can separate one or more streams containing aromatic compounds from the aromatic formation effluent. At least one of the streams containing aromatic compounds can be passed to the methylation process. A second separation process can separate one or more streams containing aromatic compounds from the methylation process. For aspects where a desired product includes xylene, a third separation can be used for separating a stream comprising the desired xylene and a stream comprising other $C_8$ compounds from one or more effluents of aromatic formation process and/or one or more effluents of the methylation process.

Controlling the amounts of benzene and toluene formed during aromatic formation has been found to improve para-xylene yield. This can be carried out by selecting the aromatic formation conditions based on one or more factors other than maximizing para-xylene yield. Accordingly, in certain aspects the aromatic formation process is operated at less than maximum xylene yield and/or para-xylene yield, e.g., ≤0.95 times the maximum of one or both of these yields, e.g., ≤0.9 times, such as ≤0.85 times, or ≤0.8 times. Instead, the overall aromatic hydrocarbon yield of the aromatics formation process is increased or maximized, resulting in an improvement in the combined yield of benzene, toluene, and xylene, and particularly an increase in the production of benzene and/or toluene and a decrease in the production of xylene. The benzene and toluene can then be converted to xylene in a subsequent methylation stage, thus providing the unexpected result that a lesser production of $C_8$ aromatic hydrocarbon during an aromatic formation process can lead to an overall increase in para-xylene produced by the method. In other aspects, the aromatics formation process is operated under conditions which decrease or even minimize the formation of ethylbenzene (another $C_8$ aromatic) during aromatics formation. Doing so lessens the need for complex and inefficient conversion of ethylbenzene to xylene, and avoids difficulties which would otherwise arise during processes downstream of the aromatic formation process, such as difficulties associated with xylene isomerization and para-xylene separation. Selecting conditions that decrease ethylbenzene selectivity during the aromatics formation process allows for an improvement in the method's overall xylene yield.

Any of the preceding aspects is compatible with adjusting the relative yield of benzene and toluene from the aromatic formation process, e.g., based on the cost and/or availability the methylating agent (e.g., methanol). For example, at locations where excess amounts of raw gas or natural gas are available, methane may be available without a high value use other than as a fuel. In such an environment, converting methane to methanol (e.g., by one or more of partial oxidation, autothermal reforming, etc.) can provide methanol at a low cost, e.g., as a low-cost methylating agent for the methylation process.

An example of a system and method suitable for converting at least a portion of the feed's non-aromatics to para-xylene while controlling the amounts of benzene and toluene formed during aromatic formation is shown in FIG. 1. At least one of the specified feeds 105 is introduced into aromatic formation process 110 for conversion of at least a portion of the selected feed's non-aromatics to aromatic hydrocarbon. In some aspects, aromatic formation process 110 can correspond to a direct conversion process, such as a dehydrocyclization or dehydroaromatization process. In other aspects, aromatic formation process 110 can represent a series of process steps, such as conversion of alkane into syngas, methanol, alkenes, or another intermediate product followed by formation of aromatic hydrocarbon from the intermediate product. Effluent 115 from aromatic formation process 110 can then be separated in an initial separation process 120, to separate from the effluent 115 at least a fraction 125 which contains at least a portion of the effluent's $C_8$ aromatic hydrocarbon, and a fraction 123 which contains at least a portion of the effluent's benzene and $C_7$ aromatic hydrocarbon. Optionally, a $C_{9+}$ stream 127 can also be separate from the effluent 115. A lower boiling (including unconverted) fraction 107 corresponding to primarily $C_{5-}$ hydrocarbon and $C_6$ non-aromatic compounds can also be separated, from the aromatic formation effluent and optionally recycled (not shown) to the aromatic formation process 110. Fraction 123 is introduced into a methylation process 130 along with a methylating agent feed 103 to produce $C_8$ aromatic hydrocarbon from benzene and $C_7$ aromatic hydrocarbon in fraction 123. The methylation effluent 135 from the methylation process 130 is conducted to a second separator 140 to separate from the methylation effluent 135 at least a fraction 145 which contains at least a portion of the methylation effluent's $C_8$ aromatic hydrocarbon and a fraction 143 which contains at least a portion of the methylation effluent's $C_6$ and $C_7$ aromatic hydrocarbon. Optionally, initial separation process 120 and second separation process 140 are combined into a single separation process, e.g., a single separation, such as by using a divided wall column separator. An example of a divided wall column separator is described in U.S. Patent Application Publication 2011/0132803, which is incorporated herein by reference with respect to its description of a divided wall column separator.

In alternative aspects, the configuration in FIG. 1 can be used for production of naphtha boiling range fuel (e.g., gasoline), such as one having a boiling range of about −1° C. to about 221° C., or 30° C. to 221° C., or 80° C. to 221° C., or 110° C. to 221° C. For example, an aromatic formation process 110 can correspond to a process that forms primarily benzene and $C_7$ aromatic hydrocarbon. In these aspects, the initial separation process 120 can be used to separate from aromatic formation effluent 115 a fraction 123 that predominantly contains benzene from aromatic formation effluent 115, and a fraction 125 that contains at least a portion of the effluent's $C_{7+}$ aromatic hydrocarbon. The benzene can then be methylated 130 to form toluene, which is a more desirable gasoline component than benzene, and in certain aspects the toluene is directly blended into gasoline. Any unreacted benzene can be recycled for further methylation. At least a portion of fraction 125 also can be used as a naphtha boiling-range fuel or fuel component.

Other aspects relate to para-xylene production methods which include providing at least a third separation zone, so that fractions derived from various reaction processes having different para-xylene concentrations are not mixed together. For example, certain systems and methods for producing para-xylene generate at least three separate $C_8$ fractions containing different concentrations of para-xylene. A first fraction can correspond to a $C_8$ fraction separated from the effluent produced by an aromatic formation process. A second fraction can correspond to a $C_8$ fraction separated from the effluent produced by a methylation process. A third fraction can correspond to a fraction derived from the effluent from a xylene isomerization process. Each of these product fractions can include different concentrations of para-xylene. Rather than combining these fractions before para-xylene separation, it has been found that it is beneficial to separately process each fraction. Although technically feasible, it can be undesirable from an equipment footprint standpoint to have a separate (e.g., physically distinct) para-xylene separation zones for each para-xylene containing fraction. More favorably, a separator having a plurality of zones is used, such as a simulated moving bed, where each fraction is introduced into a zone that is appropriate based (i) the fraction's para-xylene concentration and/or (ii) the concentration of paraxylene in the liquid phase within the zone. Fractions having a greater para-xylene concentration are typically more suitable for introduction at a zone that is proximate to the location where purified para-xylene is withdrawn from the separator.

Figure 2:
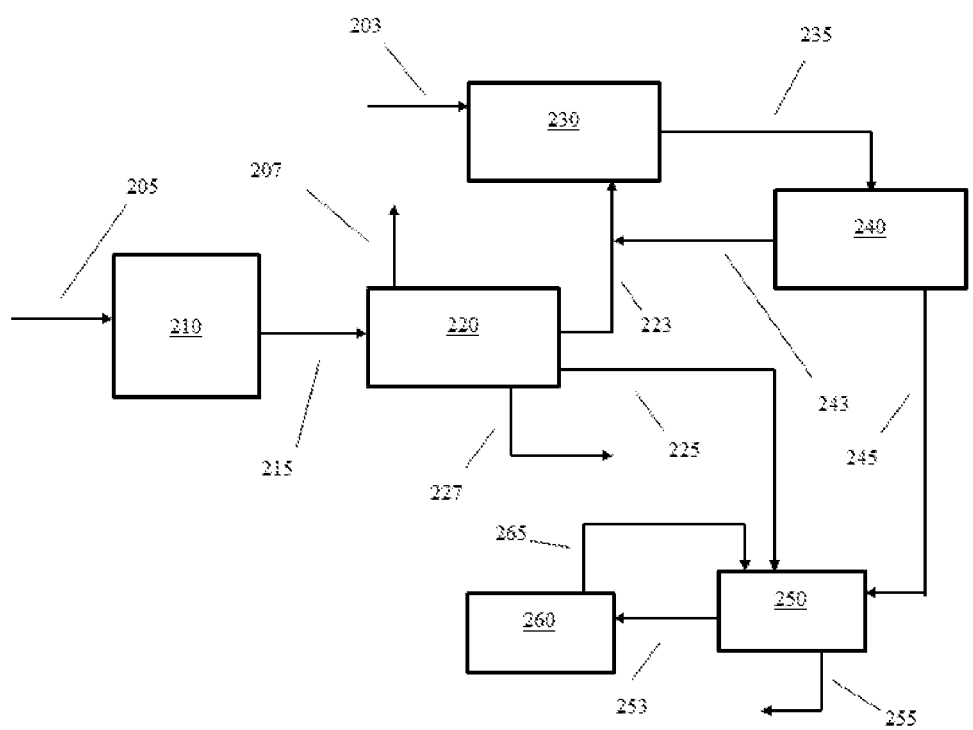
FIG. 2 schematically shows another example of a reaction system for converting a feed to form aromatic hydrocarbon.

An example of such a system is shown in FIG. 2. It is noted that similar index numbers between figures correspond to similar components. At least one of the specified feeds is introduced via conduit 205 into an aromatic formation process 210. Effluent 215 from aromatic formation process 210 is then passed into a first separation process 220, which separates at least fractions 223 and 225 from effluent 215. Fraction 225 contains at least a portion of the $C_8$ aromatic hydrocarbon from effluent 215 and fraction 223 contains at least a portion of the benzene and $C_7$ aromatic hydrocarbon from effluent 215. A lower boiling (including unconverted) fraction 207 can also be separated from effluent 215 and optionally returned (at least in part) to the aromatic formation process 210. Optionally, a stream 227 is separated from effluent 215 in first separation process 220. Stream 227 can comprise, e.g., at least a portion of any $C_{9+}$ hydrocarbons in effluent 215. In certain aspects, stream 227 comprises what remains of the effluent after the separation of fractions 223, 225, and/or 207. Fraction 223 is introduced into a methylation process 230 along with a methylating agent feed 203 (e.g., methanol) to produce $C_8$ aromatic hydrocarbon by methylating at least a portion of the benzene and/or $C_7$ aromatic hydrocarbon in fraction 223. The effluent 235 from the methylation process 230 is conducted to a second separation process 240 to separate at least fractions 243 and 245 from methylation effluent 235. Fraction 245 contains at least a portion of the $C_8$ aromatic hydrocarbon from effluent 235, and fraction 243 contains at least a portion of the benzene and $C_7$ aromatic hydrocarbon from effluent 235. Fractions 225 and 245 are passed to the third separation process 250 for separation of para-xylene from other $C_8$ aromatic hydrocarbon. In third separation process 250, a stream 255 enriched in para-xylene and a stream 253 depleted in para-xylene are separated from fractions 225 and 245. Stream 253, which is depleted in para-xylene, is passed into isomerization process 260 for conversion of ortho- and meta-xylene into para-xylene. The resulting effluent stream 265 with an increased amount of para-xylene relative to stream 253 is returned to the third separation process 250 for separation of the para-xylene. Optionally, stream 265 can be introduced into the third separation process 250 at a different separation stage than the input separation stage for stream 225, which can allow the third separation process 250 to take advantage of differing concentrations of para-xylene in stream 265 and 225. For example, a stream having a higher para-xylene concentration can be introduced into separation process 250 at a later separation stage. This can allow earlier separation stages to have a smaller processing capacity. Since the earlier separation stages in a separator correspond to stages with the largest volume (i.e., due to lower concentration of the separation target), reducing the input flows to early separation stages can reduce the required size for the potentially largest stages within a multi-stage separator. Optionally, stream 245 can be introduced into the third separation process 250 at a different stage than the input stage(s) for stream 225 and stream 265, which can allow the third separation process 250 to take advantage of differing concentrations of para-xylene in streams 225, 245, and/or 265. Alternatively, at least a portion of effluent 235 can be conducted to separation process 220, for separating streams 243 and/or 245. In other words at least part of the separation functionality of separation process 240 can be carried out in separation process 220. Optionally, first separation process 220 and second separation process 240 can be combined into a single separator and/or process, such as by using a divided wall column separator.

A particular $C_8$ aromatic has been found to be undesirable in the method, particularly in the processing of the aromatics formation effluent and the methylation effluent. The presence of ethylene benzene in the aromatics formation effluent limits the usefulness of that effluent as a feed to the methylation process. Respecting the aromatics formation effluent, conventional processes typically overcome this difficulty by additional processing of the aromatics formation effluent before methylation, e.g., dealkylation to remove the ethyl group. Respecting the methylation effluent, accumulation of ethylbenzene during liquid phase xylene isomerization is typically overcome in conventional processes by including an additional isomerization which operates in the vapor phase (typically also including a dealkylation functionality) are often selected when para-xylene is produced by a conventional method such as naphtha reforming. Certain aspects of the invention obviate the need for these costly and inefficient procedures by operating the aromatic formation process to produce an aromatics formation effluent having a decreased or even substantially minimized ethylbenzene concentration compared to that of conventional processes. For example, in certain aspects, the aromatics formation effluent has an ethylbenzene to benzene molar ratio ≤1.0, and/or a toluene to benzene molar ratio ≥1.4. Certain aspects of the invention accomplish this by utilizing a feed which comprises ≥10 wt. % of non-aromatic hydrocarbon based on the weight of the feed, e.g., ≥25 wt. %, such as ≥50 wt. %, or ≥75 wt. %, or ≥90 wt. %, or ≥95 wt. %; wherein (a) the feed's non-aromatic hydrocarbon comprises ≥50 wt. % based on the weight of the feed's non-aromatic hydrocarbon of one or more of (i) aliphatic $C_1$-$C_9$ hydrocarbon, (ii) aliphatic $C_1$-$C_9$ alkane, (iii) aliphatic $C_1$-$C_5$ alkane, (iv) one or more of methane, ethane, and propane; e.g., ≥75 wt. %, such as ≥90 wt. %, or ≥95 wt. %; and (b) the aromatic formation process feed dehydrocyclization carried out under conditions which lessen or even minimize selectivity ethylbenzene formation. When the aromatics formation process is operated under conditions which decrease or minimize ethylbenzene selectivity, the selectivity for toluene production relative to benzene can also be enhanced. Although the direct reaction products from the aromatic formation process may be lower in value (e.g., at times when benzene's value exceeds toluene's), the resulting toluene can then be methylated to form additional xylene, leading to a net improvement in the method's cost-effectiveness.

For the purpose of this description and appended claims the following terms are defined. The term "$C_n$" hydrocarbon wherein n is a positive integer, means a hydrocarbon having n number of carbon atom(s) per molecule. The terms "$C_{n+}$" hydrocarbon and "$C_{n-}$" hydrocarbon, wherein n is a positive integer, mean a hydrocarbon having at least n number of carbon atom(s) per molecule or no more than n number of carbon atom(s) per molecule, respectively. The terms "aromatics" and "aromatic hydrocarbon" mean hydrocarbon molecules containing at least one aromatic core. The term "hydrocarbon" encompasses mixtures of hydrocarbon, including those having different values of n. The term "organic oxygenate" means molecules (including mixtures of molecules) having the formula $C_nH_{2n+1}OC_mH_{2m+1}$, wherein C, H and O are carbon, hydrogen and oxygen, respectively; n is an integer having a value ≥1, e.g., in the range of from 1 to 4; and m is an integer having a value ≥zero, e.g., in the range of from zero to 4. Examples of organic oxygenate include one or more of methanol, ethanol, dimethyl ether, and diethyl ether. The term "syngas" means a mixture comprising ≥12 mole % molecular hydrogen and ≥0.4 mole % carbon monoxide, the mole percents being per mole of the mixture.

In this description and appended claims, reference may be made to aromatics streams or fractions, e.g., those described as a $C_6$ aromatics stream or fraction, a $C_7$ aromatics stream or fraction, a $C_6$-$C_7$ aromatics stream or fraction, a $C_8$ aromatics stream or fraction, a $C_7$-$C_8$ aromatics stream or fraction, or a $C_{9+}$ aromatics stream or fraction. Each of such streams or fractions is defined to have a concentration of the named aromatic component(s) of at least 50 wt. %. Thus, a $C_6$ aromatics stream is defined herein as a stream containing at least 50 wt. % of $C_6$ aromatic compounds. Optionally, the concentration of the named aromatic component(s) can be at least 75 wt. %, or at least 90 wt. %.

Processes for conversion of alkane to aromatic hydrocarbon, as described herein, can generally be characterized as either direct conversion processes or indirect conversion processes. Direct conversion processes are defined herein as processes where the alkane-containing feed is introduced into the reaction environment where aromatic hydrocarbon is formed from non-aromatic hydrocarbon. Indirect conversion processes are defined herein as processes where the alkane-containing feed is introduced into a reaction stage different from the reaction stage where aromatic hydrocarbon is formed. For example, a reaction scheme for first converting methane to methanol and then feeding the methanol into a reaction for aromatic formation corresponds to an indirect conversion process. It is noted that a reaction scheme could correspond to both a direct and an indirect conversion process if some aromatic hydrocarbon is formed in a first process that receives the alkane-containing feed while additional aromatic hydrocarbon is formed in a second process that receives an effluent from the first process as a feed. It is noted that subsequent methylation of an existing aromatic feed does not correspond to a process for formation of aromatic hydrocarbon from non-aromatic hydrocarbon.

As used herein, an "aromatic formation" process refers to one or more processes that are used to convert non-aromatic hydrocarbon, e.g., aliphatic hydrocarbon to aromatic hydrocarbon, optionally in the presence of other components and/or co-feeds. An aromatic formation process based on a direct conversion process may encompass those having only one reactor and/or reaction stage (although multiple stages could be included). An aromatic formation process based on an indirect conversion process will typically include multiple process stages or reaction environments, since the reaction for initial conversion of the alkane occurs in a different reaction environment than the reaction for aromatic formation.

As used herein, the numbering scheme for the groups of the Periodic Table of the Elements is as disclosed in Chemical and Engineering News, 63(5), 27 (1985).

Aromatic Formation Process—General Operation

The aromatics formation process's feed typically comprises one or more $C_1$ to $C_9$ non-aromatic hydrocarbon compounds, e.g., one or more light hydrocarbon (i.e., $C_1$ to $C_5$) compounds, such as one or more paraffinic light hydrocarbon compounds. For example, the feed can comprise ≥1 wt. % based on the weight of the feed of one or more of (i) paraffinic $C_2$ to $C_9$ hydrocarbon, (ii) aliphatic $C_1$ to $C_9$ hydrocarbon, (iii) aliphatic paraffinic $C_1$ to $C_9$ hydrocarbon, (iv) paraffinic light hydrocarbon, (v) aliphatic light hydrocarbon, and (vi) aliphatic paraffinic light hydrocarbon; such as ≥10 wt. %, or ≥25 wt. %, or ≥50 wt. %, or ≥75 wt. %, or ≥90 wt. %, or ≥95 wt. %. The term "paraffinic hydrocarbon" encompasses normal, iso, and cyclo paraffin. Optionally, the feed further comprises diluent. Diluent present in the feed's source (e.g., methane and/or $CO_2$ present in natural gas) and diluent added to the feed are within the scope of the invention. Diluent, when present, is typically included in the feed in an amount ≤60 wt. % based on the weight of the feed, e.g., ≤50 wt. %, such as ≤40 wt. %, or ≤30 wt. %, or ≤20 wt. %, or ≤10 wt. %. A feed constituent is diluent when it is substantially non-reactive under the specified reaction conditions in the presence of the specified dehydrocyclization catalyst, e.g., methane, molecular nitrogen, and inert atomic gasses such as argon. Organic and inorganic diluents are within the scope of the invention.

The feed's non-aromatic $C_1$ to $C_9$ hydrocarbon can include aliphatic hydrocarbon, e.g., alkane. Representative alkane-containing feeds include those comprising at least 20 mole % of one or more $C_1$-$C_9$ alkane relative to the total number of moles in the feed, or at least 35 mole %, or at least 50 mole %, or at least 60 mole %, or at least 70 mole %, or at least 80 mole %. Additionally or alternately, the alkane-containing feedstock can initially contain at least 50 mole % of one or more $C_1$-$C_9$ alkane relative to the total number of moles of hydrocarbon in the feed, or at least 60 mole %, or at least 70 mole %, or at least 80 mole %.

The feed can include methane, e.g., ≥1 wt. % methane, such as ≥10 wt. %, or ≥20 wt. %, or ≥60 wt. %. When methane is substantially non-reactive under the specified aromatics formation reaction, the methane is considered diluent. Alternatively or in addition, the feed can comprise ethane, e.g., ≥1 wt. % ethane, based on the weight of the feed, such as ≥5 wt. %, or ≥10 wt. %, or in the range of from 10 wt. % to 40 wt. %. Suitable feeds include those containing a major amount of ethane, e.g., ≥50 wt. % ethane, such as ≥75 wt. %, or ≥90 wt. %, or ≥95 wt. %. Alternatively or in addition to the methane and/or ethane, the feed can contain $C_3$ and/or $C_4$ hydrocarbon, e.g., (i) ≥20 wt. % propane, such as ≥40 wt. %, or ≥60 wt. %, and/or (ii) ≥20 wt. % butanes, such as ≥40 wt. %, or ≥60 wt. %. In some aspects, the feed can contain a reduced amount of $C_{5+}$ hydrocarbon, e.g., ≤20 wt. %, such as ≤10 wt. %, or ≤01 wt. %. In such aspects, the feed can contain ≤10 wt. % of $C_{6+}$ saturated hydrocarbon, e.g., ≤5 wt. %.

Optionally, the feed comprises molecular hydrogen, e.g., ≥1 wt. % molecular hydrogen based on the weight of the feed, such as ≥5 wt. %. Optionally, the feed contains unsaturated $C_{2+}$ hydrocarbon, such as $C_2$-$C_5$ unsaturated hydrocarbon. When present, the amount of $C_{2+}$ unsaturated hydrocarbon (e.g., $C_2$-$C_5$ unsaturated hydrocarbon) is typically ≤20 wt. %, e.g., ≤10 wt. %, such as ≤1 wt. %, or ≤0.1 wt. %, or in the range of from 0.1 wt. % to 10 wt. %. Typically, the feed is substantially-free of aromatic hydrocarbon, where substantially-free in this context means an aromatic hydrocarbon concentration that is ≤1 wt. % based on the weight of the feed, such as ≤0.1 wt. %, or ≤0.01 wt. %, or ≤0.001 wt. %. Typically, the feed comprises a total of ≤10 wt. % of impurities such as CO, $CO_2$, $H_2S$, and total mercaptan; e.g., ≤1 wt. %, or ≤0.1 wt. %. One representative feed comprises 1 wt. % to 40 wt. % methane; ≥10 wt. % ethane, such as in the range of from 10 wt. % to 40 wt. %; 20 wt. % to 50 wt. % propane, and 20 wt. % to 50 wt. % butanes.

The feed's light hydrocarbon can be obtained from one or more sources of hydrocarbon, e.g., from natural hydrocarbon sources such as those associated with producing petroleum, or from one or more synthetic hydrocarbons sources such as catalytic and non-catalytic reactions. Examples of such reactions include catalytic cracking, catalytic reforming, coking, steam cracking, etc. Synthetic hydrocarbon sources include those in which hydrocarbon within a geological formation has been purposefully subjected to one or more chemical transformations. The feed can include components recycled from the process, e.g., from one or more locations downstream of the aromatics formation.

In certain aspects, the source of light hydrocarbon includes natural gas, e.g., raw natural gas ("raw gas"). Natural gas is (i) a mixture comprising hydrocarbon, (ii) primarily in the vapor phase at a temperature of 15° C. and a pressure of 1.013 bar (absolute), and (iii) withdrawn from a geologic formation. Natural gas can be obtained, e.g., from one or more petroleum deposits, coal deposits, and shale deposits. The natural gas can be one that is obtained by conventional production methods but the invention is not limited thereto. Raw natural gas is a natural gas obtained from a geologic formation without intervening processing, except for (i) treatments to remove impurities such as water and/or any other liquids, mercaptans, hydrogen sulfide, carbon dioxide; and (ii) vapor-liquid separation, e.g., for adjusting the relative amounts of hydrocarbon compounds (particularly the relative amounts of $C_{4+}$ hydrocarbon compounds) in the natural gas; but not including (iii) fractionation with reflux. Conventional methods can be used for removing impurities and/or adjusting the relative amount of hydrocarbon compounds present in the feed, but the invention is not limited thereto. For example, certain components in the natural gas can be liquefied by exposing the natural gas to a temperature in the range of −57° C. to 15° C., e.g., −46° C. to 5° C., such as −35° C. to −5° C. At least a portion of the liquid phase can be separated in one or more vapor-liquid separators, e.g., one or more flash drums. One suitable raw natural gas comprises 3 mole % to 70 mole % methane, 10 mole % to 50 mole % ethane, 10 mole % to 40 mole % propane, and 5 mole % to 40 mole % butanes and 1 mole % to 10 mole % of total $C_5$ to $C_9$ hydrocarbon. In certain aspects, ≥50 wt. % of the feed comprises natural gas, such as raw natural gas, e.g., ≥75 wt. %, or ≥90 wt. %, or ≥95 wt. %.

Any form of raw gas can be used as a source material, although the raw gas is typically one or more of (i) gas obtained from a natural gas well ("Gas Well", Non-associated", or "Dry" gas), (ii) natural gas obtained from a condensate well ("Condensate Well Gas"), and (iii) casing head gas ("Wet" or "Associated" gas). Table 1 includes typical raw gas compositional ranges (mole %) and, parenthetically, typical average composition (mole %) of certain raw gasses.

TABLE 1

| Component | Associated Gas | Dry Gas | Condensate Well Gas |
|---|---|---|---|
| $CO_2$ | 0-50 (0.63) | 0-25 (0) | 0-25 (0) |
| $N_2$ | 0-50 (3.73) | 0-25 (1.25) | 0-25 (0.53) |
| $H_2S$ | 0-5 (0.57) | 0-5 (0) | 0-5 (0) |
| $CH_4$ | 0-80 (64.48) | 0-97 (91.01) | 0-98 (94.87) |
| $C_2H_6$ | 5-20 (11.98) | 2-10 (4.88) | 1-5 (2.89) |
| $C_3H_8$ | 2-10 (8.75) | 0.5-5 (1.69) | 0.1-5 (0.92) |
| i-butane | 0.1-5 (0.93) | 0.05-1 (0.14) | 0.1-5 (0.31) |
| n-butane | 1-5 (2.91) | 0.05-2 (0.52) | 0.05-2 (0.22) |
| i-pentane | 0.05-2 (0.54) | 0.01-1 (0.09) | 0.01-1 (0.09) |

In certain aspects, the feed comprises ≥75 wt. % Associated Gas, based on the weight of the feed, e.g., ≥90 wt. %, or ≥95 wt. %.

The invention is therefore particularly advantageous in remote or under-developed locations, where: (i) the lack of cryogenic methane separation facilities limits the utility of conventional natural gas aromatization processes, (ii) the lack of a pipeline or natural gas production infrastructure, may result in significant quantities of light hydrocarbon being flared or burned as fuel, and (iii) Associated Gas remains stranded at a remote location for lack of pipeline facilities or a failure to meet one or more specifications of an available pipeline. Small scale plants using the present process would allow effective recovery of these light hydrocarbon resources as liquid hydrocarbons.

It is within the scope of the invention for one or more of the specified feeds to be particularly advantageous in connection with a particular aromatics formation process. Consequently, the choice of feed may depend at least in part on the aromatics formation process utilized in a particular aspect. For example, certain aspects utilize a feed comprising at least 10 mole % of particular alkane relative to the total moles of $C_1$-$C_9$ alkane in the feed, or at least 20 mole %, or at least 30 mole %, or at least 40 mole %, or at least 50 mole %, or at least 60 mole %, or at least 70 mole %, and/or up to about 100 mole % or less, or 90 mole % or less, or 80 mole % or less, or 70 mole % or less, or 60 mole % or less, or 50 mole % or less, or 40 mole % or less, or 30 mole % or less. The particular alkane can be one or more of methane, ethane, propane, or butanes, e.g., methane and ethane. Additionally or alternately, the feed can contain 50 mole % or less of $C_5$-$C_9$ alkane relative to the total moles of $C_1$-$C_9$ alkane in the feed, or 40 mole % or less, or 30 mole % or less, or 20 mole % or less, or 10 mole % or less, or the feed can be substantially free of $C_5$-$C_9$ alkane, such as 5 mole % or less, or 1 mole % or less.

As described in more detail below, the specific conditions for an aromatic formation process will depend on the nature of the process used for aromatic formation. In some aspects, any convenient aromatic formation process can be suitable. In other aspects, a suitable aromatic formation process can have one or more characteristics related to conversion of feed components; relative conversion of specific components within a feed; selectivity (i.e., yield) for one or more types of $C_8$ aromatic hydrocarbon; and/or relative selectivities for aromatic hydrocarbon.

The amount of conversion of one or more specified feed components can be used to characterize an aromatic formation process. For example, an aromatic formation process can be characterized based on conversion of $C_1$-$C_9$ alkane in a feed. The following feed conversion amounts represent conversion in a single pass. Certain aromatics formation processes convert at least 20 wt. % of particular alkane in the feed, or at least 30 wt. %, or at least 40 wt. %, or at least 50 wt. %, or at least 60 wt. %, or at least 70 wt. %, and/or up to 100 wt. % or less, or 90 wt. % or less, or 80 wt. % or less, or 70 wt. % or less, or 60 wt. % or less. Alternatively or in addition, an aromatics formation process can convert a relative amount of particular alkane. For example, in certain aromatics formation processes at least 1 wt. % of the total alkane converted in the aromatic formation process are a particular alkane, or at least 5 wt. %, or at least wt. %, or at least 20 wt. %, or at least 30 wt. %, or at least 40 wt. %, or at least 50 wt. %, and/or up to 100 wt. % or less, or 90 wt. % or less, or 80 wt. % or less, or 70 wt. % or less, or 60 wt. % or less. The particular alkane can be, e.g., (i) one or more $C_1$ to $C_9$ alkane compounds, (ii) one or more $C_1$ to $C_4$ alkane compounds, (iii) one or more $C_{5+}$ alkane compounds, and (iv) methane and/or ethane. It is noted that each of the above lower bounds for an amount of alkane conversion is explicitly contemplated with each of the above upper bounds.

The selectivity for production of benzene, $C_7$ aromatic hydrocarbon, and/or $C_8$ aromatic hydrocarbon is yet another way to characterize an aromatic formation process, e.g., the selectivity for production of benzene, $C_7$ aromatic hydrocarbon, and/or $C_8$ aromatic hydrocarbon in the aromatics formation process's effluent. For example, the amount of particular aromatic hydrocarbon in the process effluent can be 40 wt. % of the total aromatic hydrocarbon in the effluent, or at least 50 wt. %, or at least 60 wt. %, or at least 70 wt. %; or 20 wt. % or less of the total aromatic hydrocarbon in the effluent, or 10 wt. % or less, or 5 wt. % or less. The particular aromatic hydrocarbon can be one or more $C_6$ to $C_8$ aromatic hydrocarbon compounds, e.g., (i) $C_8$ aromatic hydrocarbon, and/or (ii) $C_6$-$C_7$ aromatic hydrocarbon. More particularly, an aromatic formation process can be characterized based on the selectivity for production of one or more particular $C_8$ aromatic hydrocarbon relative to the total amount of $C_8$ aromatic hydrocarbon in the process effluent. For example, the amount of ethylbenzene in the process effluent can be 30 wt. % or less relative to the total $C_8$ aromatic hydrocarbon in the effluent, or 25 wt. % or less, or 20 wt. % or less, or 15 wt. % or less, or 10 wt. % or less. Additionally or alternately, the amount of ethylbenzene in the effluent can be 25 wt. % or less relative to the total $C_6$-$C_8$ aromatic hydrocarbon in the effluent, or 20 wt. % or less, or 15 wt. % or less, or 10 wt. % or less. In aspects where para-xylene is separated from other $C_8$ aromatic hydrocarbon, a reduced or minimized ethylbenzene concentration can allow for use of a liquid isomerization process as part of a para-xylene recovery loop and/or can reduce or minimize the amount of purge required from such a liquid isomerization process.

Yet another way to characterize an aromatic formation process is based on the selectivity for production of $C_7$ aromatic hydrocarbon relative to the amount of benzene produced. In certain aspects, the molar ratio of $C_7$ aromatic hydrocarbon (toluene) to the amount of $C_6$ aromatics (benzene) can be at least 1.0, or at least 1.4, or at least 1.5, or at least 1.8, or at least 2.0, or at least 2.5. Typically benzene is a higher value product, and therefore performing an aromatic formation process to enhance toluene yield is unconventional. In other aspects, the molar ratio of $C_7$ aromatic hydrocarbon (toluene) to benzene can be 1.0 or less, or 0.9 or less, or 0.8 or less, or 0.7 or less, or 0.6 or less.

Factors such as (i) relative value of toluene to benzene, and/or (ii) the relative cost of the inputs to the aromatic formations process and the methylation process can be used in selecting a particular molar ratio. For example, as the relative value of toluene increases, the aromatic formation conditions can be altered to generate higher ratios of toluene to benzene. Another option can be to select an increased molar ratio of $C_7$ aromatic hydrocarbon to $C_6$ aromatic hydrocarbon to lessen the formation of olefin and/or other side products during methylation. Converting benzene to toluene during methylation requires reaction conditions with increased severity relative to conversion of toluene to xylene. This can lead to additional formation of side products during methylation, and potentially can also require increased amounts of recycle of $C_6$-$C_7$ components.

In aspects where at least a portion of the methane in the feed is converted to methanol, controlling the relative amounts of toluene and benzene can provide further benefits. Depending on the relative cost of methane and the relative cost of the methanol production step within the aromatic formation process, the aromatic formation conditions can be selected to provide a net improved yield of xylene relative to the amount of carbon in the feed. For example, aromatic formation conditions that lower production of xylene can also tend to reduce or minimize ethylbenzene formation. Subsequent methylation of benzene or toluene to form $C_8$ aromatic hydrocarbon also tends to lead to reduced or minimized concentrations of ethylbenzene. If the cost of producing methanol is low relative to the other feed components for aromatic formation, increasing the amount of xylene formed by methylation of toluene and/or benzene can be a beneficial way to add carbon for formation of $C_8$ aromatic hydrocarbon while reducing or minimizing the ethylbenzene concentration.

Examples of Aromatic Formation Processes

Examples of suitable conversion processes for forming aromatic hydrocarbon from non-aromatic hydrocarbon include oxidative coupling methods; co-conversion of methane with co-reactants; reforming of alkane to form syngas, which can then be converted directly to aromatic hydrocarbon or converted via formation of an intermediate such as a methanol or another oxygenate; dehydroaromatization of $C_{3+}$ alkane; conversion of ethane or larger alkane to aromatic hydrocarbon in presence of metal activated ZSM-5 or ZSM-11; conversion of methane on Mo ZSM-5 or any molybdenum carbide type catalyst; or others.

Indirect Processes

One indirect process includes converting methane (and/or other alkane) to aromatic hydrocarbon. For example, alkane can be reformed to form CO, $CO_2$, $H_2O$, and $H_2$ (i.e., syngas), and the syngas can then be used to synthesize a variety of larger compounds. The molar ratio of $H_2$ to CO generated during reforming can depend on the type of reforming, such as higher ratios of $H_2$ to CO for steam reforming. The syngas can be produced by any convenient method, including conventional methods such as the partial oxidation of methane and/or the steam reforming of methane. Suitable methods include those described in U.S. Patent Application Publication Nos. 2007/0259972 A1, 2008/0033218 A1, and 2005/0107481, each of which is incorporated by reference herein in its entirety. The resulting syngas can then, for example, be converted to $C_{2+}$ alkane using a Fischer-Tropsch type reaction. Such $C_{2+}$ compounds can then be converted to aromatic hydrocarbon, such as using one or more of the processes identified herein.

In other indirect processes, the syngas is converted to methanol and/or dimethyl ether (DME). The methanol and/or DME are then converted to aromatic hydrocarbon in an aromatics conversion process. For example, the conversion of syngas to methanol (or other alcohols) can be carried out at very high selectivity using a mixture of copper, zinc oxide, and alumina at a temperature of 200° C. to 400° C. and pressures of 50-500 atm. In addition to $Cu/ZnO/Al_2O_3$, other catalyst systems suitable for methanol synthesis include $Zn/VCr_2O_3$, $Cu/ZnO$, $Cu/ZnO/Cr_2O_3$, $Cu/ThO_2$, $CoS_x$, $MoS_x$, Co—$MoS_x$, Ni—S, Ni—$MoS_x$, and Ni—Co—$MoS_x$.

Suitable processes for converting methanol and/or DME to aromatic hydrocarbon include the MTG (methanol to gasoline) process. The MTG process is disclosed in the patent art, including, for example, U.S. Pat. Nos. 3,894,103; 3,894,104; 3,894,107; 4,035,430; and 4,058,576. U.S. Pat. No. 3,894,102 discloses the conversion of synthesis gas to gasoline. MTG processes provide a simple means of converting syngas to high-quality gasoline. The ZSM-5 catalyst used is highly selective to gasoline under methanol conversion conditions, and is not known to produce distillate range fuels, because the $C_{10+}$ olefin precursors of the desired distillate are rapidly converted via hydrogen transfer to heavy polymethylaromatics and $C_4$ to $C_8$ isoparaffins under methanol conversion conditions.

More generally, conversion of methanol (and/or dimethyl ether) to aromatic hydrocarbon can be performed using as a catalyst a composition of matter comprising a molecular sieve and a Group 8-14 element, or a molecular sieve and a combination of metals from the same group of the Periodic Table. The composition of matter can optionally further comprise phosphorus and/or lanthanum and/or other elements from Group 1-2 and/or Group 13-16 of the Periodic Table that provide structural stabilization. Many examples of conversion of methanol and/or olefin to aromatic hydrocarbon are conventionally known, such as the processes described in U.S. Patent Application Publication 2015/0175499, the entirety of which is incorporated herein by reference.

An example of a suitable catalyst for conversion of $C_{2+}$ or $C_{3+}$ alkane can be a medium pore molecular sieve, such as ZSM-5, that includes both a) Zn as a supported metal or in the catalyst framework and b) phosphorus as a supported metal. The catalyst can correspond to a bound or substantially binder-free catalyst. The ZSM-5, ZSM-11, or other medium pore zeolite can include about 0.1 wt. % to about 5 wt. % of Zn and about 0.1 wt. % to about 5 wt. % of P. A feed containing $C_1$-$C_9$ alkane can be exposed to the catalyst for conversion of alkane to aromatic hydrocarbon under conditions similar to those noted above for dehydroaromatization. It is noted that for processes including conversion of $C_{2+}$ alkane and/or conversion of oxygenates, both benzene and toluene can typically be produced in substantial quantities. In such aspects, the relative amounts of benzene and toluene produced can be dependent on the reaction conditions, so that the relative amounts of benzene and toluene produced can be controlled.

Direct Processes

Suitable direct processes for aromatics formation include the conventional catalytic reforming of heavy naphtha. Since such reforming tends to have a relatively high selectivity for ethylbenzene formation as compared to other forms of aromatization, the following methods may have greater utility in the practice of the invention.

Certain suitable direct processes for aromatics formation include methane dehydrocyclization. Although methane is abundant, the relative inertness of methane has conventionally limited its utility in direct conversion processes for producing higher-value hydrocarbon. This difficulty can be at least partially overcome using methods described in U.S. Pat. No. 8,378,162, the entirety of which is incorporated herein by reference. The disclosed methods include converting methane (and optionally other alkane compounds) by a non-oxidative aromatization process at elevated temperatures, such as greater than about 700° C. or greater than about 800° C. Such processes typically produce an aromatic product comprising primarily benzene, with little or no production of $C_{7+}$ aromatic hydrocarbon, such as para-xylene. For example, such processes typically exhibit (i) a benzene to toluene molar ratio of at least about 8:1, or at least about 10:1, or at least about 15:1, or at least about 20:1; and/or (ii) benzene to ethylbenzene molar ratio of at least about 10:1, or at least about 15:1, or at least about 20:1, or at least about 30:1. Optionally, a portion of a natural gas feed (or other methane-containing feed) used for direct conversion of methane to aromatic hydrocarbon can also be used for methanol production, so that a single feed source can provide methanol for a subsequent alkylation stage to form para-xylene from the benzene generated by methane conversion. Other suitable direct processes for methane dehydrocyclization utilize a co-reactant. For example, U.S. Pat. No. 5,936,135 discloses reacting methane at a temperature in the range of 300° C. to 600° C. with (i) a $C_{2-10}$ olefin, and/or (ii) a $C_{2-10}$ paraffin in the presence of a bifunctional pentasil zeolite catalyst, having strong dehydrogenation and acid sites, to produce aromatic hydrocarbon. The preferred mole ratio of olefin and/or higher paraffin to methane and/or ethane in the feed ranges from about 0.2 to about 2.0. The use of organic oxygenate as a co-reactant is disclosed in U.S. Pat. No. 7,022,888. The organic is represented by a general formula: $C_nH_{2n+1}OC_mH_{2m+1}$, wherein C, H and O are carbon, hydrogen and oxygen, respectively; n is an integer having a value between 1 and 4; and m is an integer having a value between zero and 4. The methane and oxygenate are converted to $C_{2+}$ hydrocarbon, particularly to gasoline range $C_6$-$C_{10}$ hydrocarbon and hydrogen, using a bifunctional pentasil zeolite catalyst, having strong acid and dehydrogenation functions, at a temperature below 700° C.

Alternatively, or in addition to methane aromatization, certain suitable direct processes for aromatics formation include aromatization of $C_{2+}$ hydrocarbon, e.g., those carried out under relatively mild conditions compared to those needed for methane aromatization. For example, U.S. Pat. No. 4,788,364 (incorporated herein by reference with regard to the description of a catalyst and general reaction conditions for aromatic formation), describes a method for conversion of $C_2$-$C_{10}$ alkane to aromatic hydrocarbon in the presence of a conversion catalyst and optionally further in the presence of an olefin co-feed. The catalyst can include a molecular sieve such as ZSM-5, ZSM-11, ZSM-12, ZSM-22, and/or ZSM-35. The catalyst can further include a catalytic metal such as P, Ga, Sn, Re, Zn, Pt, and/or Cu, which can be incorporated by ion exchange, impregnation by incipient wetness, or any other convenient method. The reaction can occur in two zones, with dehydrogenation to form olefins and aromatic hydrocarbon in a first zone, and oligomerization and further dehydrocyclization occurring in a second zone. The reaction is performed at a pressure of 50 to 2000 kPa, with a temperature in the first zone of 537° C. to 895° C. and a temperature in the second zone of 215° C. to 535° C. A riser reactor can be a convenient configuration for providing the desired reaction conditions for the two zones while using a catalyst compatible for catalyzing the reaction in both zones. Converting $C_{3+}$ non-aromatic hydrocarbon, e.g., $C_{3+}$ alkane, to aromatic hydrocarbon can be accomplished under relatively less severe conditions than conversion of methane or $C_2$ hydrocarbon, such as by using a dehydroaromatization process. An example of a dehydroaromatization process is described in U.S. Pat. No. 5,043,502. Briefly, an alkane-containing feed can be exposed to a catalyst at a temperature of about 350° C. to about 650° C., or about 400° C. to about 550° C., a pressure of about 1 to about 20 atmospheres, or about 2 to about 10 atmospheres, and a liquid hourly space velocity (LHSV) of about 0.2 to about 5.0 $hr^{-1}$, or about 0.5 to about 2.0 $hr^{-1}$. The catalyst can correspond to a medium pore zeolite, such as ZSM-5, that also includes a gallium component. At higher temperature conditions, the process can also allow for some ethane conversion. More generally, $C_{2+}$ alkane can be converted to aromatic compounds based on exposure of an alkane containing feed to a medium pore molecular sieve, such as ZSM-5 or ZSM-11. The medium pore molecular sieve can be one that a supported catalytic metal and/or incorporates an additional metal component such as Ga and/or Zn.

The invention will now be described with respect to a particular aromatics formation process which includes the dehydrocyclization of $C_{2+}$ non-aromatic hydrocarbon, e.g., $C_2$-$C_9$ non-aromatic hydrocarbon, such as $C_2$-$C_9$ paraffinic hydrocarbon, or raw gas. The invention is not limited to these aspects, and this description is not meant to foreclose the use of other aromatics formation processes within the broader scope of the invention. In this form of dehydrocyclization, a feed, e.g., one comprising raw gas, is reacted in the presence of a catalytically effective amount of at least one dehydrocyclization catalyst located in at least one reaction zone operating under catalytic dehydrocyclization conditions. The reaction converts at least a portion of the feed's $C_2$-$C_9$ non-aromatic hydrocarbon to aromatic hydrocarbon and molecular hydrogen. Typically, the dehydrocyclization catalyst comprises ≥10 wt. % of a molecular sieve component and ≥0.005 wt. % of a dehydrogenation component. When the molecular sieve component and dehydrogenation component together comprise less than 100 wt. % of the catalyst, ≥90 wt. % of the remainder of the catalyst can comprise a matrix component, such as ≥99 wt. % of the remainder. The catalyst typically comprises the molecular sieve component in an amount ≥20 wt. %, based on the weight of the catalyst, e.g., ≥25 wt. %, such as in the range of from 30 wt. % to 99.9 wt. %. In certain aspects, the molecular sieve component comprises aluminosilicate, e.g., ≥90 wt. % of at least one aluminosilicate. The aluminosilicate can be an un-substituted aluminosilicate, a substituted aluminosilicate, or a combination thereof.

The molecular sieve component typically comprises ≥90 wt. % of one or more of the specified molecular sieves, e.g., ≥95 wt. %. In certain aspects, the molecular sieve component comprises at least one zeolite molecular sieve, e.g., ≥90 wt. % zeolite, such as ≥95 wt. %, based on the weight of the molecular sieve component. Although the molecular sieve component can consist essentially of or even consist of zeolite, in alternative aspects the zeolite(s) is present in the molecular sieve component in combination with other (e.g., non-zeolitic) molecular sieve. The zeolite can be one that is in hydrogen form, e.g., one that has been synthesized in the alkali metal form, but is then converted from the alkali to the hydrogen form. Typically the zeolite is one having a medium pore size and a Constraint Index of 2-12 (as defined in U.S. Pat. No. 4,016,218). Examples of suitable zeolites include ZSM-5, ZSM-11, ZSM-12, ZSM-22, ZSM-23, ZSM-35, ZSM-48, including and mixtures and intermediates thereof, such as ZSM-5/ZSM-11 admixture. Optionally, the zeolite is one comprising at least one set of pores of substantially uniform size extending through the molecular sieve, wherein geometric mean of the cross-sectional dimensions of each of the sets of pores is >5 Å, or >5.3 Å, e.g., ≥5.4 Å, such as ≥5.5 Å, or in the range of 5 Å to 7 Å, or 5.4 Å to 7 Å. ZSM-5 and/or ZSM-12 are suitable, particularly H-ZSM-5. For example, the molecular sieve component can comprise ≥90 wt. % of (A) ZSM-5 and/or (B) ZSM-12, based on the weight of the molecular sieve component, e.g., ≥95 wt. % of H-ZSM-5. In certain aspects, the molecular sieve has a relatively small crystal size, e.g., small crystal ZSM-5, meaning ZSM-5 having a crystal size ≤0.05 µm, such as in the range of 0.02 µm to 0.05 µm. Small crystal ZSM-5 and the method for determining molecular sieve crystal size are disclosed in U.S. Pat. No. 6,670,517, which is incorporated by reference herein in its entirety.

In other aspects, the molecular sieve component comprises at least one molecular sieve of the MCM-22 family, e.g., MCM-22 alone or in combination with other molecular sieve, such as one or more of the specified zeolites. As used herein, the term "molecular sieve of the MCM-22 family" (or "material of the MCM-22 family" or "MCM-22 family material" or "MCM-22 family zeolite") includes one or more of: a) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference); b) molecular sieves made from a common second degree building block, being a 2-dimensional tiling of such MWW framework topology unit cells, forming a monolayer of one unit cell thickness, preferably one c-unit cell thickness; c) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof and d) molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures thereof. Related zeolite UZM-8 is also suitable for use as the molecular sieve component.

When the molecular sieve component comprises at least one aluminosilicate, e.g., at least one zeolite, the aluminosilicate's silica:alumina ratio (substantially the same as the aluminosilicate's Si:Al$_2$ atomic ratio) is typically ≥2, e.g., in the range of from 5 to 100. The silica:alumina ratio is meant to represent the Si:Al$_2$ atomic ratio in the rigid anionic framework of the crystalline aluminosilicate. In other words, aluminum in (i) any matrix or binder or (ii) in cationic or other form within the crystalline aluminosilicate's channels is excluded from the silica:alumina ratio. Alternatively or in addition, the catalyst can be made more resistant to deactivation (and increase aromatic hydrocarbon yield) by including phosphorous with the molecular sieve component. Conventional methods can be utilized for adding phosphorous, but the invention is not limited thereto. When used, the amount of phosphorous is typically ≥1 wt. % based on the weight of the molecular sieve component. For example, when the molecular sieve component comprises aluminosilicate, the phosphorous:aluminum atomic ratio can be in the range of from 0.01 to 1. Zeolite having a higher silica:alumina ratio can be utilized when a lower catalyst acidity is desired, e.g., in the range of from 44 to 100, such as from 50 to 80, or 55 to 75.

In addition to the molecular sieve component, the catalyst comprises ≥0.005 wt. %, based on the weight of the catalyst, of a dehydrogenation component, e.g., at least one dehydrogenation metal. The dehydrogenation component can comprise one or more neutral metals selected from Groups 3 to 13 of the Periodic Table of the Elements, such as one or more of Ga, In, Zn, Cu, Re, Mo, W, La, Fe, Ag, Pt, and Pd, and/or one or more oxides, sulfides and/or carbides of these metals. For example, the dehydrogenation component can be Ga, Zn, or a combination thereof, optionally supported on a catalyst comprising ZSM-5 as the molecular sieve component. Typically, the catalyst comprises ≥0.01 wt. % of the dehydrogenation component, based on the weight of the catalyst. Those skilled in the art will appreciate that when the dehydrogenation component comprises one or more metals of greater catalytic dehydrogenation activity, e.g., Pt, and/or Pd, a lesser amount of dehydrogenation component is needed, e.g., in the range of 0.005 wt. % to 0.1 wt. %, based on the weight of the catalyst, such as 0.01 wt. % to 0.6 wt. %, or 0.01 wt. % to 0.05 wt. %. When the dehydrogenation component comprises one or more metals of lesser dehydrogenation activity, e.g., one or more of Ga, In, Zn, Cu, Re, Mo, and W, a greater amount of dehydrogenation component is needed, e.g., in the range of 0.05 wt. % to 10 wt. %, based on the weight of the catalyst, such as 0.1 wt. % to 5 wt. %, or 0.5 wt. % to 2 wt. %.

Besides the molecular sieve component and dehydrogenation component, the catalyst can further comprise an optional matrix component, e.g., one or more inorganic binders. A matrix component can be used, e.g., to make the catalyst more resistant to the temperatures and other conditions employed in the conversion reaction. The amount of matrix component is not critical. When present, the amount of matrix component is typically in the range of 0.01 times the weight of the molecular sieve component to about 0.9 times the weight of the molecular sieve component, e.g., in the range of 0.02 to 0.8. The matrix component can include active materials, such as synthetic or naturally occurring zeolites. Alternatively, or in addition, the matrix component can include clays and/or oxides such as alumina, silica, silica-alumina, zirconia, titania, magnesia or mixtures of these and other oxides. The matrix component can include naturally occurring materials and/or materials in the form of gelatinous precipitates or gels including mixtures of silica and metal oxides. Clays may also be included with the oxide type binders to modify the mechanical properties of the catalyst or to assist in its manufacture. Alternatively or in addition, the matrix component can include one or more substantially inactive materials. Inactive materials suitably serve as diluents to control the amount of conversion so that products may be obtained economically and orderly without employing other means for controlling the rate of reaction. Alternatively or in addition to any phosphorous added to or impregnated into the molecular sieve component, the matrix component can optionally include phosphorous, e.g., to lessen catalyst acidity. The matrix component is optional.

The catalyst can be one that has been subjected to one or more treatments, e.g., a selectivation treatment to increase selectivity for producing desired aromatic hydrocarbon compounds such as para-xylene. For example, the selectivation can be carried out before introduction of the catalyst into the reactor and/or in-situ in the reactor, e.g., by contacting (optionally a plurality of times) the catalyst with a selectivating agent, such as at least one organosilicon in a liquid carrier and subsequently calcining the catalyst at a temperature of 350 to 550° C. Such a selectivation process is described in detail in U.S. Pat. Nos. 5,633,417 and 5,675,047, which are incorporated by reference herein in their entirety.

Typically, the catalyst has a surface area as measured by nitrogen physisorption in the range of from 100 $m^2/g$ to 600 $m^2/g$, e.g., in the range of from 200 $m^2/g$ to 500 $m^2/g$. When the catalyst comprises aluminosilicate which includes phosphorous, the phosphorous:aluminum atomic ratio is typically in the range of from 0.01 to 0.5. For example, the catalyst can contain ≥10 wt. % of phosphorous-modified alumina, such as ≥15 wt. %, or in the range of from 10 wt. % to 20 wt. %.

The dehydrocyclization is carried out in the presence of at least one of the specified dehydrocyclization catalysts, which is typically located in at least one bed within a dehydrocyclization reaction zone. Conventional fixed, moving, and/or fluidized beds can be used in the dehydrocyclization reaction zone, but the invention is not limited thereto.

During dehydrocyclization, at least a portion of the feed is exposed to a catalytically effective amount of the specified dehydrocyclization under catalytic dehydrocyclization conditions that are effective for converting at least a portion of the feed's $C_1$-$C_9$ non-aromatic hydrocarbon to aromatic hydrocarbon and molecular hydrogen. The catalytic dehydrocyclization conditions can include exposing the feed to a temperature in the range of from 400° C. to 800° C., a pressure in the range of from 100 kPa to 2200 kPa. Typically, the catalytic dehydrocyclization conditions further include a space velocity (WHSV) ≥0.1 $hr^{-1}$. More typically, the catalytic dehydrocyclization conditions include a temperature in the range of from 400° C. to 750° C., such as 400° C. to 700° C., or 400° C. to 650° C., or 500° C. to 625° C., a pressure in the range of from 30 psia (207 kPa) to 80 psia (522 kPa). Space velocity (WHSV) can be in the range of from 0.1 $hr^{-1}$ to 20 $hr^{-1}$. Typically, the space velocity (WHSV) of $C_{2+}$ hydrocarbon (the "$C_{2+}$ WHSV") in the specified raffinate with respect to the second catalyst is in the range of from 0.1 $hr^{-1}$ to 20 $hr^{-1}$, e.g., 0.2 $hr^{-1}$ to 5 $hr^{-1}$, or 0.3 $hr^{-1}$ to 1 $hr^{-1}$. The $C_{2+}$ WHSV is the hourly rate of the $C_{2+}$ hydrocarbon (in grams per hour) exposed to the second catalyst per gram of the second catalyst. The reaction is typically endothermic. Generally, the average temperature drop across the reaction zone is ≤600° C., more typically in the range of from 20° C. to 200° C., e.g., in the range of from 50° C. to 150° C.

It has been found that it is beneficial for the dehydrocyclization catalyst to have a residence time of ≤90 seconds in the dehydrocyclization reaction zone under dehydrocyclization conditions. It has been discovered that doing so dramatically increases the conversion of $C_{2+}$ hydrocarbon without a significant decrease in the selectivity for aromatic hydrocarbon, and without excessive selectivity for light hydrocarbon compounds such as methane. More particularly, it has been found that it is beneficial for the dehydrocyclization catalyst to have a residence time in the reaction zone under dehydrocyclization conditions of ≤60 seconds, e.g., ≤30 seconds, such as ≤10 seconds, or ≤1 second, or ≤0.1 second or in the range of from 0.001 second to 60 seconds. Especially when the catalyst is present in a moving bed and/or fluidized bed, it is beneficial for the dehydrocyclization catalyst to have a residence time in the dehydrocyclization reaction zone that is in the range of from 0.01 second to 10 seconds, e.g., 0.1 second to 10 seconds, such as 0.1 second to 1 second. After the specified residence time, the dehydrocyclization catalyst is typically at least partially regenerated and then returned to dehydrocyclization service. The regeneration can be carried out in the reaction zone. Alternatively or in addition, the dehydrocyclization catalyst can be removed from the reaction zone after the specified residence time, at least partially regenerated outside of the reaction zone, and then returned to the reaction zone for continued dehydrocyclization after the regeneration.

Initial Separation Process for Separation of Aromatic Formation Effluent

The effluent from the aromatic formation process can be conducted to a first separation process for separation of one or more streams or fractions from the effluent. The initial or first separation process can include one or more separation stages based on boiling point (distillation) differences within the effluent. Optionally, for feeds including a substantial portion of $C_{6+}$ alkane, a solvent separation stage may also be provided for separation of $C_{6+}$ alkane from $C_{6+}$ aromatic products.

Generally, the effluent from aromatic formation can include aromatic hydrocarbon, unreacted feed, and optionally additional non-aromatic reaction products. Most of the components in the effluent can be conveniently separated based on distillation methods. The particular types of streams formed during separation can be dependent on the nature of the aromatic formation process.

In some aspects, the effluent from an aromatic formation process can include substantial amounts (such as more than 10 vol. %, or more than 20 vol. %) of $C_6$-$C_8$ aromatic hydrocarbon, or $C_6$-$C_8$ aromatic hydrocarbon and $C_{9+}$ aromatic hydrocarbon. In such aspects, a distillation can allow for separation from the aromatic formation effluent of at least a $C_6$-$C_7$ aromatics stream, a $C_8$ aromatics stream, a (optional) $C_{9+}$ aromatics stream, optionally an unreacted feed stream and/or a hydrogen stream, and optionally one or more additional non-aromatic reaction product streams. Depending on the nature of the separation process, the $C_{9+}$ aromatics stream or another product stream can alternatively correspond to a remaining portion of the effluent after separation of other streams. As defined previously, the named aromatic hydrocarbon component ($C_6$-$C_7$; $C_8$; and $C_{9+}$) for a stream corresponds to at least 50 wt. % of the aromatic hydrocarbon concentration in the stream, or at least 75 wt. %, or at least 90 wt. %. The $C_8$ stream (or at least a portion of the $C_8$ stream) can be sent to a subsequent separation process for separation of a para-xylene enriched stream. The $C_6$-$C_7$ stream (or at least a portion of the $C_6$-$C_7$ stream) can be sent to a methylation process for conversion of at least a portion of the $C_6$-$C_7$ components to $C_8$ components. The $C_{9+}$ stream can be withdrawn from the reaction system, exposed to a dealkylation process to generate additional benzene for introduction into the methylation stage, exposed to a transalkylation process to generate additional $C_8$ aromatic hydrocarbon for introduction into the xylene separation zone, and/or handled in any other convenient manner. Optionally, a portion of the unreacted feed can be recycled to the aromatic formation process.

In some alternative aspects, it may be desirable to separate a $C_6$ stream and a $C_7$ stream from the aromatic formation effluent to allow for removal of a portion of the benzene stream as a product. Additionally or alternately, this can be desirable during production of naphtha boiling range fuels or fuel components, so that at least a portion of the benzene can be selectively methylated to form toluene.

In other aspects, the output from the effluent from the aromatic formation process may contain substantial amounts of $C_6$-$C_7$ aromatic hydrocarbon, while having a reduced or minimized concentration of $C_8$ aromatic hydrocarbon and/or $C_{9+}$ aromatic hydrocarbon. In such aspects, a distillation can allow for separation from the aromatic formation effluent of at least a $C_6$ aromatics (i.e., benzene) stream, a $C_7$ aromatics stream, an unreacted feed stream and/or a hydrogen stream, and optionally a stream of non-aromatic reaction products. In yet other aspects, the effluent from the aromatic formation process may contain substantial amounts of $C_6$ aromatic hydrocarbon, methane (or other unreacted feed), and hydrogen, while having a reduced or minimized amount of other aromatic components. In such aspects, the initial separation stage can separate at least a $C_6$ aromatics stream, an unreacted feed stream, and/or a hydrogen stream from the aromatic formation effluent.

Methylation of Aromatic Hydrocarbon

At least a portion of a $C_6$ stream, $C_7$ stream, or $C_6$-$C_7$ stream separated from the aromatic formation effluent in the first separation process can optionally be used as a product stream, as both benzene and toluene are commercially valuable. Another option can be to use at least a portion of a $C_6$ stream, $C_7$ stream, or $C_6$-$C_7$ stream separated from the aromatic formation effluent as a feed for a methylation process. A methylation process can form $C_8$ compounds by reacting $C_6$ and/or $C_7$ compounds with a methylating agent, such as methanol, dimethyl ether (DME), methyl bromide, and/or methyl chloride. Methylation processes typically provide a high selectivity for forming xylenes in preference to ethylbenzene. An example of a process for the selective production of para-xylene by exposing benzene and/or toluene to methanol under effective catalytic conditions is described in U.S. Pat. No. 8,344,197, which is incorporated herein by reference. Additionally or alternately, a methylation process can be used for production of toluene from benzene.

Temperature is an important parameter in the reaction of benzene and/or toluene with a methylating agent. Because temperatures between 450° C. and 700° C. are beneficial for improving or maximizing conversion, the aromatic feed and methylating agent feed are preheated before being supplied to the methylation process, with the exothermic heat generated by the methylation reaction generally being sufficient to maintain the reaction temperature at the desired value. In practice, however, there are limits on the temperatures to which the different feeds can be preheated. For example, in the case of the benzene/toluene feed, the preheating temperature is limited by the coking rates in the preheater which, depending on factors such as heat flux, stream composition and heat transfer surface metallurgy, will generally be about 550° C. In the case of the methylating agent feed, decomposition to carbon oxides, hydrogen and methane will generally limit the preheating temperature to about 220° C.

Generally, the conditions employed in a methylation process can include a temperature between 450° C. and 700° C., or about 550° C. to about 650° C.; a pressure between 14 psig and 1000 psig (between 100 and 7000 kPa), or between 10 psig and 200 psig (between 170 and 1480 kPa); a molar ratio of aromatic to methanol in the reactor charge of at least 0.2, such as from 2 to 20; and a weight hourly space velocity ("WHSV") for total hydrocarbon feed to the reactor(s) of 0.2 to 1000 $hr^{-1}$, or 0.5 to 500 $hr^{-1}$ for the aromatic reactant, and 0.01 to 100 $hr^{-1}$ for the methylating agent, based on total catalyst in the reactor(s).

The methylation process can employ any aromatic feedstock comprising toluene and/or benzene. Optionally, the aromatic feed can contain at least 90 weight %, especially at least 99 weight %, of benzene, toluene or a mixture thereof. The composition of the methylating agent feed is not critical. Optionally, it can be beneficial to employ feeds containing at least 90 weight %, especially at least 99 weight %, of a methylating agent. The methylation process can produce a methylation effluent having a weight of $C_8$ aromatic hydrocarbon of at least 70% of a weight of $C_8$ aromatic hydrocarbon in the aromatic formation effluent, or at least 90%, or at least 100%, or at least 150%, or at least 200%.

The catalyst for methylation can be a porous crystalline material. The porous crystalline material is preferably a medium-pore size aluminosilicate zeolite. Medium pore zeolites are generally defined as those having a pore size of about 5 to about 7 Angstroms, such that the zeolite sorbs molecules such as n-hexane, 3-methylpentane, benzene and p-xylene. Another common definition for medium pore zeolites involves the Constraint Index test which is described in U.S. Pat. No. 4,016,218, which is incorporated herein by reference. In this case, medium pore zeolites have a Constraint Index of about 1-12, as measured on the zeolite alone without the introduction of oxide modifiers and prior to any steaming to adjust the diffusivity of the catalyst. In addition to the medium-pore size aluminosilicate zeolites, other medium pore acidic metallosilicates, such as silicoaluminophosphates (SAPOs), can be used in the present process.

Particular examples of suitable medium pore zeolites include ZSM-5, ZSM-11, ZSM-12, ZSM-22, ZSM-23, ZSM-35, and ZSM-48, with ZSM-5 and ZSM-11 being particularly preferred. In one embodiment, the zeolite employed in the process of the invention is ZSM-5 having a silica to alumina molar ratio of at least 250, as measured prior to any treatment of the zeolite to adjust its diffusivity.

Second Separation Zone

The methylation process produces an effluent that can be separated to form one or more output streams based on boiling point or distillation. In aspects where xylene production occurs (such as para-xylene production), a first output stream separated from a methylation effluent can be an unreacted $C_6$-$C_7$ stream (possibly including $C_7$ compounds that formed due to methylation of $C_6$), which can be at least partially recycled to the methylation. A second output stream separated from the methylation effluent can correspond to a lower boiling point stream, including unreacted methanol and other $C_5-$ reaction products. A third output stream separated from the methylation effluent can correspond to a $C_8$ aromatics stream. Optionally, one of the first output stream, second output stream, or third output stream can correspond to a remaining portion of the methylation effluent after separation of other output streams.

Although both the aromatic formation process and the methylation process can generate similar product streams (e.g., a $C_8$ aromatics stream, a $C_6$-$C_7$ product stream, etc.), in various aspects different separation processes are employed for separation of the methylation effluent and the aromatic formation effluent. While it is possible that the methylation effluent and the aromatic formation effluent could have substantially the same ratios of $C_8$ products in the respective $C_8$ aromatics streams, more typically the $C_8$ aromatics streams produced from the aromatic formation process and the methylation process will have different compositions. This can include differences in both the concentration of para-xylene and the concentration of ethylbenzene. The differences in the concentration of para-xylene between $C_8$ aromatics streams can be exploited to provide an improved para-xylene separation process. Streams having a greater para-xylene concentration, e.g., the $C_8$ aromatics stream conducted away from the second separator, can be kept segregated from streams having a lesser para-xylene concentration. Processing the segregated streams in distinct separation stages and/or in distinct zones within a separation stage has been found to beneficially (i) increase the efficiency of para-xylene separation, (ii) increase para-xylene yield, and/or (iii) decrease the size, capacity, and/or complexity of the xylene separation stages and zones compared to separations that are carried out with the streams combined.

One option for performing distinct separations on the effluents from the aromatic formation process and the methylation process can be to use a divided wall column separator. Conventional divided wall column separators can be used, e.g., those that include separate volumes and a common volume. The separate volumes in the divided wall column separator are divided by a wall, with the height of the wall being selected so that products having a sufficiently low boiling range can enter a common volume of the separator. This can allow for formation of multiple high boiling range products while generating a single low boiling range output. During operation, two (or more) segregated streams can be each introduced into a separated or distinct volume of the divided wall column separator. As the effluent is distilled, the higher boiling portions of the streams remain segregated due to the dividing wall. The lower boiling portions can travel up the column of the separator into the common volume, where one or more common lower boiling fractions can be removed. The wall in the separator can provide any convenient configuration for the separated or otherwise segregated volumes. For example, the wall can correspond to a chord (such as a diameter) that bisects the typically circular shaped distillation column, or a wall that forms concentric separated volumes.

Additionally or alternately, in some aspects the operation of the first separation process and second separation process can be different based on the different types of effluent streams being separated. For example, if a $C_6$ aromatics stream and a $C_7$ aromatics stream are separated from the aromatic formation effluent in the first separation stage, a reduced or minimized amount of benzene will be present in that portion of the $C_7$ aromatics stream which is passed into the methylation process. This typically results in an effluent from the methylation stage that comprises $C_7$ aromatic hydrocarbon and $C_8$ aromatic hydrocarbon in a total amount greater than about 50 wt. %, but comprises less than about 25 wt. % benzene. In this type of configuration, the second separation process can be considerably simplified, e.g., to remove an extract comprising greater than 90 wt. % of the methylated effluent's $C_7$ aromatic hydrocarbon and greater than 90 wt. % of any benzene in the methylated effluent. A raffinate comprising substantially all of the methylated effluent's $C_8$ aromatic hydrocarbon is conducted away for para-xylene recovery.

Third Separation Zone (Xylene Separation)

Typically, distillation is not an effective method for separation of para-xylene from other xylenes and/or ethylbenzene. Instead, para-xylene is typically separated from a $C_8$ aromatic fraction or stream by other convenient methods, such as by selective adsorption or crystallization. Conventional xylene separation processes can be used, e.g., moving beds and simulated moving beds, but the invention is not limited thereto. Any convenient number of feed input and/or product output locations can be used, with 4 to 30 locations being typical. For example, in a xylene separation process that includes twenty four input locations, the isomerized effluent from xylene isomerization can be introduced into the first location. The $C_8$ aromatic stream separated from either the aromatic formation effluent or the methylation effluent can then be introduced at any other convenient location based on the concentration of para-xylene in the $C_8$ stream.

U.S. Pat. Nos. 5,750,820 and 8,529,757 (each of which is incorporated herein by reference in its entirety) describe selective adsorption methods which can be referred to as a simulated moving bed.

The description below describes operation of a simulated moving bed based on a simplified conceptual example. In this example, the number of zones is equal to the minimum number needed to show the different simulated moving bed processes at the same time. Those of skill in the art will recognize that more generally any number of zones can be included in a simulated moving bed separator. Generally, any convenient number of feed and/or output locations can be provided for the simulated moving bed. During operation, the different input streams and output streams for the simulated moving bed can be rotated through the feed and/or output locations to simulate the effect of having a moving bed separator.

In aspects where $C_8$ aromatic streams or fractions of varying para-xylene concentration are available, the $C_8$ output streams can be introduced into the simulated moving bed as separate feeds at different relative locations. For example, the effluent from the xylene isomerization process can be introduced into a simulated moving bed at a conventional location (the first location), e.g., a location downstream (with respect to fluid flow) of the location (the second location) at which purified para-xylene is extracted from the simulated moving bed. For the $C_8$ streams derived from the aromatic formation effluent and/or the methylation effluent, one or more input locations that are positioned between the first and second location can be selected, e.g., based on the para-xylene concentration of each respective effluent. This can optionally allow the $C_8$ stream separated from the aromatic formation effluent and/or the methylation effluent to be introduced into the simulated moving bed separator at a location where the para-xylene concentration in the fluid undergoing separation in the simulated moving bed at the input location approximately corresponds to the para-xylene concentration in the aromatic formation effluent or methylation effluent. This decreases or even minimizes the required volume for the separator, as the $C_8$ streams with higher para-xylene concentration can be introduced at locations in the simulated moving bed which are relatively close to the location at which purified para-xylene is extracted. Advantageously, doing so lessens the volume of input flows with lower para-xylene purity, which would otherwise require increased bed volume and/or energy for para-xylene separation.

Additionally or alternately, a portion of the aromatic formation effluent and/or the methylation effluent can be used as a flush stream for the input lines to the simulated moving bed. Because the entry and exit locations of the various streams in a simulated moving bed are constantly changing, the input and output lines for the simulated moving bed can contain streams of various purity. To avoid mixing a higher purity stream with a lower purity stream, flushing of the input and output lines can be performed. For example, when flushing an output line prior to withdrawal of high purity para-xylene product from the simulated moving bed, it is beneficial to first flush the stream with an intermediate purity stream followed by a flush stream having a para-xylene concentration comparable to the desired output. The higher para-xylene concentrations in an aromatic formation effluent and/or a methylation effluent can be suitable for use as an intermediate purity stream during flushing of the input and/or output lines.

In a simulated moving bed, the movement of tray(s) or bed(s) of solid sorbent may be simulated by use of a system of conduits which permits directing and redirecting the streams of fluids into the chamber at different separation zones at different times. As these stream changes occur, the solid sorbents are employed in different steps in an adsorption process as though the solids were moving through the chamber.

The different zones within an adsorption apparatus or system are defined by the particular step of the adsorption process performed within each zone, e.g., (1) an adsorption step in the adsorption zone; (2) a purification step in the purification zone; (3) a desorption step in the desorption zone. These terms have the same meaning as the description of these terms from U.S. Pat. No. 5,750,820. Briefly, in the adsorption zone, the input fluid comes into contact with the adsorbent material, and the desired component(s) are adsorbed by the solid sorbent which comprise material that is active for the desired sorbtion (the "active material"). After adsorption, a purification stream is fed into the active material to flush the unwanted components from the active material, e.g., from within and from the interstitial areas between the solid sorbent. This results in a raffinate stream containing unwanted components that can be flushed from the purification zone. After the solid sorbent has been subjected to the purification stream, the stream in the conduit(s) may again be changed to introduce a desorbent steam (such as a high purity para-xylene stream) into the chamber to release the product.

Within each of the above zones, multiple inputs and/or outputs may also be present. For example, in the adsorption zone a first input stream can correspond to a lower concentration para-xylene stream. A second input stream can also be introduced within the adsorption zone, but at a location that is typically downstream (with respect to fluid flow in the simulated moving bed) of the first input stream, e.g., at a location where the liquid-phase concentration profile (see e.g., FIG. 1 of U.S. Pat. No. 5,750,820) of para-xylene in the adsorption zone approximately corresponds to the concentration of para-xylene in the second input stream.

Figure 3:
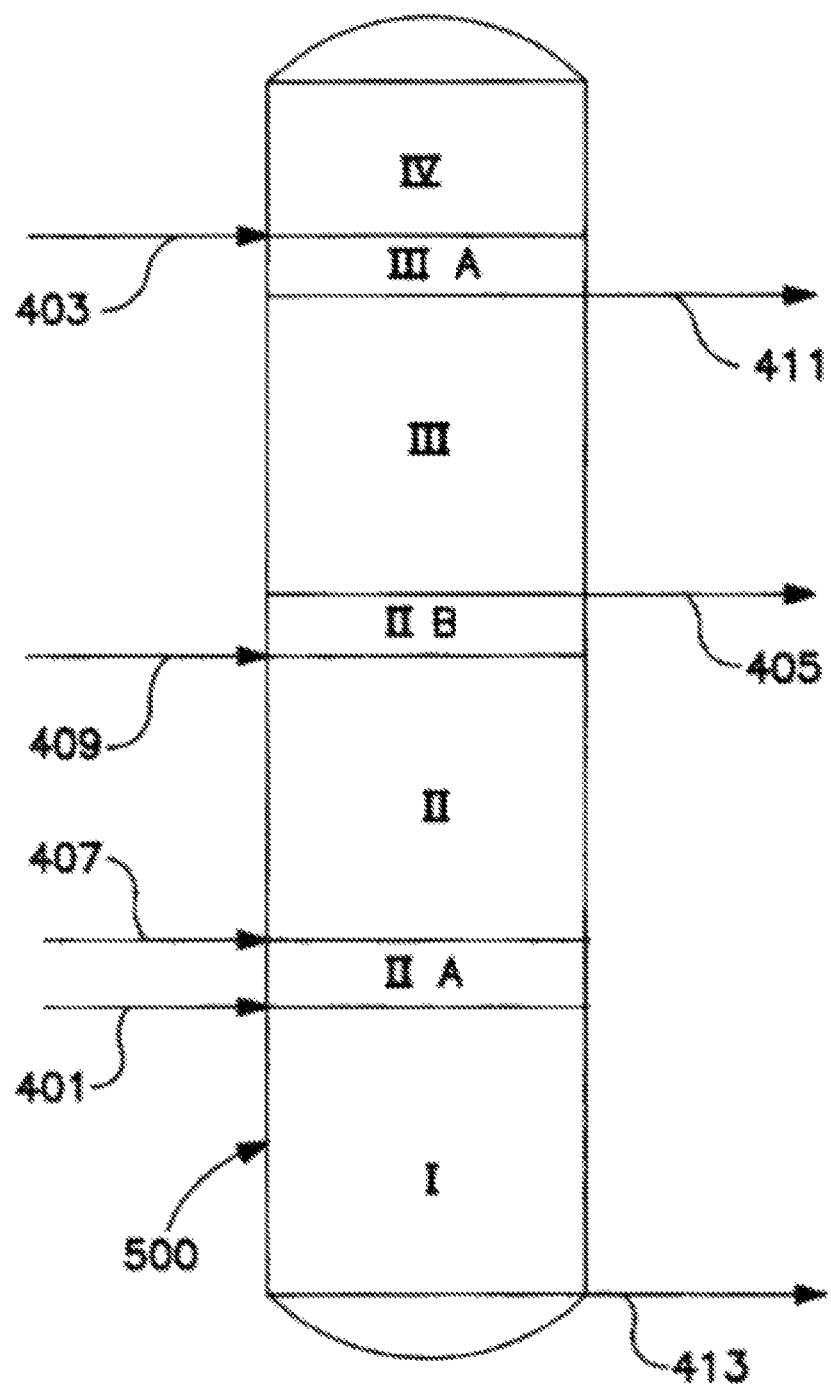
FIG. 3 schematically shows an example of a simulated moving bed separator.

FIG. 3 schematically shows an example of a suitable simulated moving bed, including the locations of various adsorption, desorption, and purification zones. The zones shown in FIG. 3 represent the location of the zones at a particular instant in time. Rather than moving solid sorbent through these various zones, the inputs and outputs to the simulated moving bed can be varied so that the zones move relative to the solid sorbent instead of having the solid sorbent move relative to the zones. In FIG. 3, zone I corresponds to an adsorption zone, zone II corresponds to a purification zone, zone III corresponds to a desorption zone, and zone IV corresponds to a buffer zone to maintain separation between the desorption zone and the adsorption zone. It is noted that FIG. 3 also shows sub-zones IIA, IIB, and IIIA. These additional sub-zones represent additional feed entry and/or output exit locations. In various aspects, any convenient number of additional input and/or output locations can be used, to allow for additional input streams, additional flush streams, or additional output streams from a simulated moving bed.

In FIG. 3, chamber 500 is fed by feed fluid communication conduit 401 (corresponding to the input for adsorption zone I), desorbent fluid communication conduit 403, flushing fluid communication conduit 407, and secondary flushing fluid communication conduit 409. Extract fluid communication conduit 405 (corresponding to the desired high purity para-xylene product), flushing fluid communication conduit 411, and raffinate fluid communication conduit 413 (corresponding to a para-xylene depleted output stream) lead from chamber 500. The input stream in conduit 401 can correspond to, for example, the output from the para-xylene isomerization stage. The flushing fluids introduced by conduits 407 and 409 can correspond to input streams having an intermediate para-xylene concentration relative to the concentration of the input stream in conduit 401 and the extract stream in conduit 405. These flushing streams can drive unwanted components from the bed and lines so that a stream with increased para-xylene concentration can subsequently be extracted from the bed. The higher para-xylene concentration streams generated from aromatic formation and/or methylation can be introduced here, or they can be introduced at still other locations within the simulated moving bed based on the concentration of the streams relative to the concentration profile in the simulated moving bed. Flushing output 411 corresponds to an intermediate concentration output stream relative to the concentration of the input stream in conduit 401 and the extract stream in conduit 405.

Xylene Isomerization

Typically xylene streams found in chemical or petrochemical plants also contain ethylbenzene. Conventional isomerization technologies operating at high temperatures (e.g., 400° C.) in vapor phase isomerize the xylenes and dealkylate ethylbenzene to benzene. Other vapor-phase isomerization technologies convert ethylbenzene to xylenes in addition to xylenes isomerization. There are also liquid-phase isomerization technologies.

For the methods described herein, both vapor phase isomerization and liquid phase isomerization can be suitable for isomerization of the para-xylene depleted stream from a para-xylene separation process. For aromatic formation processes other than naphtha reforming and/or pyrolysis, a $C_8$ aromatics stream separated from the aromatic formation process can have a reduced ethylbenzene concentration. In some aspects, the reduced amount of ethylbenzene in $C_8$ aromatics streams separated from an aromatic formation effluent and/or methylation effluent can allow for reduced severity during vapor phase isomerization. In some aspects, the reduced amount of ethylbenzene in $C_8$ aromatic streams separated from the aromatic formation effluent and/or methylation effluent can allow for use of liquid phase isomerization for some or all of the isomerization of the para-xylene depleted stream from the para-xylene separation stage.

U.S. Pat. No. 8,697,929 describes an example of a liquid phase isomerization system, the entirety of which is incorporated herein by reference. Briefly, liquid phase isomerization of xylenes can be performed at a temperature of less than 295° C. and a pressure sufficient to maintain the xylenes in liquid phase. In certain aspects, the isomerization utilizes a catalyst comprising a zeolite, preferably at least one selected from the group consisting of ZSM-5 and MCM-49. In embodiments, the process utilizes a catalyst comprising ZSM-5 along with a binder or the ZSM-5 may be substantially binder-free. Optionally, the catalyst can be characterized by one or more of the following characteristics: the ZSM-5 is in the proton form (HZSM-5); the ZSM-5 has a crystal size of less than 0.1 microns; the ZSM-5 has a mesoporous surface area (MSA) greater than 45 $m^2/g$; the ZSM-5 has a zeolite surface area (ZSA) to mesoporous surface area (MSA) ratio of less than 9; a silica to alumina weight ratio in the range of 20 to 50.

The isomerization typically produces very low level of by-products, such as less than 1 wt. % or preferably less than 0.5 wt. % of by-products selected from non-aromatic compounds, benzene and $C_{9+}$ aromatic hydrocarbon, and mixtures thereof.

Typically, liquid phase isomerization includes contacting a feedstream comprising $C_8$ aromatic hydrocarbons with a catalyst suitable for isomerization at a temperature below 295° C., preferably below 280° C., and at a pressure sufficiently to keep the reactant in liquid phase. One of skill in the art would be able to determine other operating characteristics, such as a lower temperature, within which the present invention may be practiced. Lower limits may be, for instance, above 180° C. or 190° C. or 200° C., or 210° C., and the like. The flow rate can be selected by one of ordinary skill in the art in possession of the present disclosure, but may advantageously be selected within the range from 1 to 100 weight hourly space velocity (WHSV), preferably from 1 to 20 WHSV, and more preferably from 1 to 10 WHSV.

Example—Integrated Use of Methanol Derived from Natural Gas or Raw Gas

In some aspects, a methane-containing feed can be at least partially converted to methanol, such as by forming a syngas intermediate or by partial oxidation. In such aspects, the methanol generated from the methane-containing feed can be used as feed or co-feed for the aromatic formation process, as an input for the methylation process, or a combination thereof. This can allow for flexibility in selecting the conditions in the aromatic formation process. For example, the aromatic formation process conditions can be selected to have a low selectivity for ethylbenzene formation relative to other types of aromatic hydrocarbon. This may reduce the yield of total aromatic hydrocarbon from the aromatic formation process, but a recycle loop can be used to allow the net yield of aromatic hydrocarbon to be increased while maintaining a low selectivity for ethylbenzene relative to other aromatic hydrocarbon. The benzene and $C_7$ aromatic hydrocarbon produced in the aromatic formation process can then be methylated using the methanol derived from the same methane/methanol source used for aromatic formation.

While the present invention has been described with respect to certain aspects, it is to be understood that the invention is not limited to the particulars disclosed and extends to all equivalents within the scope of the claims. Unless otherwise stated, all percentages, parts, ratios, etc., are by weight. Unless otherwise stated, a reference to a compound or component includes the compound or component by itself as well as in combination with other elements, compounds, or components, such as mixtures of compounds. Further, when an amount, concentration, or other value or parameter is given as a list of upper preferable values and lower preferable values, this is to be understood as specifically disclosing all ranges formed from any pair of an upper preferred value and a lower preferred value, regardless of whether ranges are separately disclosed. All patents, test procedures, and other documents cited herein, including priority documents, are fully incorporated by reference to the extent such disclosure is not inconsistent and for all jurisdictions in which such incorporation is permitted.

The invention claimed is:

1. A method for forming aromatic compounds, comprising:

providing a feed comprising non-aromatic hydrocarbon, the feed's non-aromatic hydrocarbon comprising $C_1$-$C_9$ alkane, at least 50 wt. % of the feed's non-aromatic hydrocarbon comprising $C_1$-$C_2$ alkane;

producing an aromatic formation effluent comprising benzene, $C_7$ aromatic hydrocarbon, and ≤10 wt. % of $C_8$ aromatic hydrocarbon from at least a portion of the feed's non-aromatic hydrocarbon in an aromatic formation process carried out under effective aromatic formation conditions, the aromatic formation process including converting at least 20 wt. % of the feed's $C_1$-$C_9$ alkane;

separating from the aromatic formation effluent a first $C_8$ intermediate stream and a first lower boiling intermediate stream, the first $C_8$ intermediate stream having a $C_8$ aromatic hydrocarbon concentration (weight percent) greater than that of the aromatic formation effluent, the first lower boiling intermediate stream having a benzene concentration (weight percent), a $C_7$ aromatic hydrocarbon concentration (weight percent), or a combined $C_6$-$C_7$ aromatic hydrocarbon concentration (weight percent) greater than those of the aromatic formation effluent;

reacting at least a portion of the first lower boiling intermediate stream with a methylating agent in the presence of a zeolite catalyst to form a methylated intermediate stream, the methylated intermediate stream having a $C_8$ aromatic hydrocarbon concentration (weight percent) greater than that of the portion of the first lower boiling intermediate stream which reacts to form the methylated intermediate stream;

separating from the methylated intermediate stream a second $C_8$ intermediate stream and a second lower boiling intermediate stream, the second $C_8$ intermediate stream having a $C_8$ aromatic hydrocarbon concentration (weight percent) greater than that of the methylated intermediate stream;

separating from the first $C_8$ intermediate stream, the second $C_8$ intermediate stream, or a combination thereof (a) a first para-xylene enriched fraction from the first $C_8$ intermediate stream, the first para-xylene enriched fraction having a para-xylene concentration (weight percent) greater than that of the first $C_8$ intermediate stream, (b) a second para-xylene enriched fraction from the second $C_8$ intermediate stream, the second para-xylene enriched fraction having a para-xylene concentration (weight percent) greater than that of the second $C_8$ intermediate stream, and (c) a para-xylene depleted fraction, the separations (a), (b), and (c) being carried out in a common separation process;

isomerizing at least a portion of the para-xylene depleted fraction to form an isomerized product stream, wherein the portion of the para-xylene depleted fraction subjected to the isomerization has a para-xylene concentration (weight percent) less than that of the isomerized product stream; and separating a third para-xylene enriched fraction from the isomerized product stream, the third para-xylene enriched fraction having a para-xylene concentration (weight percent) greater than that of the isomerized product stream.

2. The method of claim 1, wherein the first lower boiling intermediate stream is a $C_6$-$C_7$ aromatics stream.

3. The method of claim 1, wherein the first lower boiling intermediate stream is a $C_7$ aromatics stream, the method further comprising separating a $C_6$ aromatics stream from the aromatic formation effluent.

4. The method of claim 1, wherein (a) benzene and $C_7$ aromatic hydrocarbon together constitute at least 50 wt. % of the total aromatic hydrocarbon in the aromatic formation effluent and/or (b) the aromatic formation effluent comprises 10 wt. % or less of $C_8$ aromatic hydrocarbon.

5. The method of claim 1, wherein the aromatic formation process includes at least one of (a) at least 5 wt. % of the non-aromatic hydrocarbon converted in the aromatic formation process is methane, (b) at least 10 wt. % of the non-aromatic hydrocarbon converted in the aromatic formation process is ethane, at least 20 wt. % of the non-aromatic hydrocarbon converted in the aromatic formation process is $C_1$-$C_4$ alkane, and (d) 50 wt. % or less of the non-aromatic hydrocarbon converted in the aromatic formation process is $C_5$-$C_9$ alkane.

6. The method of claim 1, further comprising determining a first relative valuation of toluene to benzene, and determining a second relative valuation of the feed's non-aromatic hydrocarbon to the methylation agent.

7. The method of claim 6, further comprising preselecting the effective aromatic formation conditions to produce an aromatic formation effluent having a toluene to benzene molar ratio ≥1.4 when the first relative valuation is greater than 1.0 and/or the second relative valuation is less than 1.0.

8. The method of claim 1, wherein (a) the separating of (i) the first $C_8$ intermediate stream and the first lower boiling intermediate stream from the aromatic formation effluent and (ii) the second $C_8$ intermediate stream and the second lower boiling intermediate stream from the methylated intermediate stream, are carried out in a divided wall separator, (b) the second lower boiling intermediate stream is combined with the first lower boiling intermediate stream before the reacting at least a portion of the first lower boiling intermediate stream with the methylating agent, and (c) the first $C_8$ intermediate stream is not combined with the second $C_8$ intermediate stream before the common separation process.

9. The method of claim 8, wherein the common separation process comprises a common simulated moving bed separation process.

10. The method of claim 9, wherein the separation of the third para-xylene enriched fraction from the isomerized product stream is carried out in the common separation process.

11. The method of claim 10, wherein at least a portion of the first $C_8$ intermediate stream and/or at least a portion of the second $C_8$ intermediate stream is introduced into the common simulated moving bed separator at a different location than that of the isomerized product stream.

12. The method of claim 10, wherein at least a portion of the first $C_8$ intermediate stream, at least a portion of the second $C_8$ intermediate stream, or a combination thereof is introduced into the common simulated moving bed separator as a flushing stream.

13. The method of claim 1, wherein (a) the methylated intermediate stream's $C_8$ aromatic hydrocarbon concentration (weight percent) is ≥$Z_1$ times the aromatic formation effluent's $C_8$ aromatic hydrocarbon concentration (weight percent) and (b) $Z_1$ is equal to 0.7, or 0.9, or 1.0, or 1.5, or 2.0.

14. The method of claim 1, wherein ≥90 wt. % of the portion of the para-xylene depleted product subjected to the isomerizing is in the liquid phase during the isomerizing.

15. The method of claim 1, wherein the aromatic formation effluent includes ≤10 wt. % ethylbenzene based on the total weight of aromatic hydrocarbon in the aromatic formation effluent, and/or the aromatic formation effluent includes ≤20 wt. % ethylbenzene based on the weight of $C_6$-$C_8$ aromatic hydrocarbon in the aromatic formation effluent.

16. The method of claim 1, further comprising:
separating a $C_{9+}$ intermediate stream from the aromatic formation effluent;
exposing at least a portion of the $C_{9+}$ intermediate stream to a transalkylation catalyst under effective transalkylation conditions to form a transalkylation effluent, the transalkylation effluent having $C_8$ aromatic hydrocarbon concentration (weight percent) that is greater than that of the portion of the $C_{9+}$ intermediate stream which is subjected to the transalkylation; and
separating a third $C_8$ intermediate stream and a third lower boiling intermediate stream from the transalkylation effluent, the third $C_8$ intermediate stream having a $C_8$ aromatic hydrocarbon concentration (weight percent) that is greater than that of the transalkylation effluent.

17. The method of claim 1, further comprising separating from the aromatic formation effluent a light aliphatic product stream comprising one or more aliphatic alkane, one or more aliphatic olefins, or a combination thereof; the feed further comprising at least a portion of the light aliphatic product stream.

18. The method of claim 1, further comprising converting methane to synthesis gas and/or methanol, wherein the formation of the methylated intermediate stream is carried out in the presence of at least a portion of the converted synthesis gas and/or methanol.

19. The method of claim 18, wherein at least a portion of the converted synthesis gas and/or methanol is a co-feed to the aromatic formation process.

* * * * *